US007518016B2

(12) United States Patent
Dieterle et al.

(10) Patent No.: US 7,518,016 B2
(45) Date of Patent: Apr. 14, 2009

(54) LONG-TERM OPERATION OF A HETEROGENEOUSLY CATALYZED GAS PHASE PARTIAL OXIDATION OF AT LEAST ONE ORGANIC COMPOUND

(75) Inventors: Martin Dieterle, Mannheim (DE); Gerhard Laqua, Kapellen (BE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 623 days.

(21) Appl. No.: 11/121,986

(22) Filed: May 5, 2005

(65) Prior Publication Data

US 2005/0261517 A1 Nov. 24, 2005

Related U.S. Application Data

(60) Provisional application No. 60/572,124, filed on May 19, 2004.

(30) Foreign Application Priority Data

May 19, 2004 (DE) ........................ 10 2004 025 445

(51) Int. Cl.
*C07C 51/16* (2006.01)
(52) U.S. Cl. ..................................... 562/545
(58) Field of Classification Search ................. None
See application file for complete search history.

(56) References Cited

U.S. PATENT DOCUMENTS

| 3,702,259 | A | 11/1972 | Nielsen |
| 3,799,886 | A | 3/1974 | Felice et al. |
| 3,956,377 | A | 5/1976 | Dolhyj et al. |
| 4,077,912 | A | 3/1978 | Dolhyj et al. |
| D267,485 | S | 1/1983 | Robinson |
| 4,408,079 | A | 10/1983 | Merger et al. |
| 4,496,770 | A | 1/1985 | Duembgen et al. |
| 5,173,468 | A | 12/1992 | Boehning et al. |
| 5,221,767 | A | 6/1993 | Boehning et al. |
| 5,231,226 | A | 7/1993 | Hammon et al. |
| 5,264,625 | A | 11/1993 | Hammon et al. |
| 5,668,077 | A | 9/1997 | Klopries et al. |
| 5,734,068 | A | 3/1998 | Klopries et al. |
| 6,410,785 | B1 | 6/2002 | Zehner et al. |
| 6,781,017 | B2 * | 8/2004 | Machhammer et al. ..... 568/470 |
| 2004/0015013 | A1 | 1/2004 | Hammon et al. |
| 2004/0181083 | A1 | 9/2004 | Proll et al. |
| 2005/0096483 | A1 | 5/2005 | Dieterle et al. |

FOREIGN PATENT DOCUMENTS

| DE | 1 254 137 | 11/1967 |
| DE | 2 025 430 | 12/1971 |
| DE | 2 159 346 | 6/1972 |
| DE | 2 106 796 | 8/1972 |
| DE | 2 351 151 | 4/1974 |
| DE | 25 26 238 | 1/1976 |
| DE | 0 058 927 A1 | 9/1982 |
| DE | 0 092 097 A1 | 10/1983 |
| DE | 40 22 212 A1 | 1/1992 |
| DE | 41 32 263 A1 | 4/1993 |
| DE | 41 32 684 A1 | 4/1993 |
| DE | 43 11 608 A1 | 12/1994 |
| DE | 199 02 562 A1 | 7/2000 |
| DE | 100 28 582 A1 | 12/2001 |
| DE | 100 46 672 A1 | 3/2002 |
| DE | 102 32 748 | 7/2002 |
| DE | 101 31 297 A1 | 1/2003 |
| DE | 103 50 822 | 6/2005 |
| EP | 0 372 972 | 6/1990 |
| EP | 0 522 871 A1 | 1/1993 |
| EP | 0 529 853 A2 | 3/1993 |
| EP | 0 608 838 A2 | 8/1994 |
| EP | 0 614 872 A1 | 9/1994 |
| EP | 0 990 636 A1 | 4/2000 |
| EP | 1 090 684 A1 | 4/2001 |
| EP | 1 106 598 A2 | 6/2001 |
| EP | 1 180 508 A1 | 2/2002 |
| GB | 1 291354 | 10/1972 |
| GB | 1 464 198 | 2/1977 |
| WO | WO 89/07101 | 8/1989 |
| WO | WO 01/96270 A2 | 12/2001 |

OTHER PUBLICATIONS

Yu Liu, et al., "Effect of pressure on oxidative coupling of methane over $MgO/BaCO_3$ catalyst-studies of its deactivation at elevated pressure", Applied Catalysis A: General, vol. 168, No. 1, XP-004271343, Mar. 13, 1998, pp. 139-149.

J. Hagen, "Industrial Catalysis, 4.5 Catalyst Deactivation and Regeneration [6]", Wiley-VCH, Weinheim, Germany, XP-002337788, 1999, pp. 180-192.

Prof. Dr. Hans Beyer, Lehrbuch Der Organischen Chemie, 1973, p. 261.

\* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process for the long-term operation of a heterogeneously catalyzed gas phase partial oxidation of at least one organic compound over a catalyst bed, in which, in order to counteract the deactivation of the catalyst bed, the working pressure in the gas phase is increased during the operating time of the catalyst bed.

12 Claims, 8 Drawing Sheets

LONG-TERM OPERATION OF A HETEROGENEOUSLY CATALYZED GAS PHASE PARTIAL OXIDATION OF AT LEAST ONE ORGANIC COMPOUND

The present invention relates to a process for the long term operation of a heterogeneously catalyzed gas phase partial oxidation of at least one organic compound in at least one oxidation reactor, in which a starting reaction gas mixture comprising the at least one organic compound, molecular oxygen and at least one inert diluent gas is passed through at least one catalyst bed at elevated temperature.

A complete oxidation of an organic compound with molecular oxygen means here that the organic compound is converted under the reactive action of molecular oxygen in such a way that all of the carbon present in the organic compound is converted to oxides of carbon and all of the hydrogen present in the organic compound to oxides of hydrogen. All different conversions of an organic compound under the reactive action of molecular oxygen are summarized here as partial oxidations of an organic compound.

In particular, partial oxidations shall refer here to those conversions of organic compounds under the reactive action of molecular oxygen in which the organic compound to be partially oxidized, on completion of conversion, contains at least one more oxygen atom in chemically bound form than before the partial oxidation was carried out.

A diluent gas which behaves substantially inertly under the conditions of the heterogeneously catalyzed gas phase partial oxidation refers to those diluent gases whose constituents remain unchanged under the conditions of the heterogeneously catalyzed gas phase partial oxidation, each constituent being viewed alone, to an extent of more than 95 mol %, preferably to an extent of more than 99 mol %.

BACKGROUND OF THE INVENTION

It is commonly known that partial and heterogeneously catalyzed oxidation of a very wide range of organic compounds using molecular oxygen in the gas phase allows numerous basic chemicals to be obtained. Examples include the conversion of propylene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 92097, EP-A 58927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene, p-xylene or naphthalene to phthalic anhydride (cf., for example, EP-A 522 871) or the corresponding acids, and also the conversion of butadiene to maleic anhydride (cf., for example, DE-A 21 06 796 and DE-A 16 24 921), the conversion of n-butane to maleic anhydride (cf., for example, GB-A 14 64 198 and GB 12 91 354), the conversion of indanes to, for example, anthraquinone (cf., for example, DE-A 20 25 430), the conversion of ethylene to ethylene oxide or of propylene to propylene oxide (cf., for example, DE-B 12 54 137, DE-A 21 59 346, EP-A 372 972, WO 89/0710, DE-A 43 11 608 and Beyer, Lehrbuch der organischen Chemie [Textbook of organic chemistry], 17th edition (1973), Hirzel Verlag, Stuttgart, p. 261), the conversion of propylene and/or acrolein to acrylonitrile (cf., for example, DE-A 23 51 151), the conversion of isobutene and/or methacrolein to methacrylonitrile (i.e. the term partial oxidation in this document shall also include partial ammoxidation, i.e. a partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 10 13 1297, EP-A 1090 684, EP-A 608 838, DE-A 10 04 6672, EP-A 529 853, WO 01/96270 and DE-A 10 02 8582), the conversion of isobutane to methacrolein and/or methacrylic acid, and also the reactions of ethane to give acetic acid, of ethylene to give ethylene oxide, of benzene to give phenol, and also of 1-butene or 2-butene to give the corresponding butanediols, etc.

The catalysts used are normally in the solid state.

Particularly frequently, the catalysts used are oxide catalysts or are noble metals (e.g. Ag). In addition to oxygen, the catalytically active oxide composition may comprise only one other element or more than one other element (multielement oxide compositions). Particularly frequently, the catalytically active oxide compositions used are those which comprise more than one metallic element, in particular more than one transition metal. In this case, reference is made to multimetal oxide compositions. Typically, multielement oxide compositions are not simple physical mixtures of oxides of the elemental constituents, but rather heterogeneous mixtures of complex poly compounds of these elements.

Usually, heterogeneously catalyzed gas phase partial oxidations, in particular those mentioned above, are carried out at elevated temperature (generally a few hundred ° C., typically from 100 to 600° C.).

Since most heterogeneously catalyzed gas phase partial oxidations proceed highly exothermically, for reasons of heat removal, they are appropriately carried out frequently in a fluidized bed or in isothermal fixed bed reactors where they are disposed in a reaction chamber around which a heat exchange medium is passed for the purpose of indirect heat exchange (for example, the catalyst bed may be disposed as a fixed bed in the catalyst tubes of a tube bundle reactor around which a salt melt is conducted for heat removal).

However, heterogeneously catalyzed gas phase partial oxidations may in principle also be carried out in catalyst beds disposed in adiabatic reactors.

It is known that the working pressure (absolute pressure) in heterogeneously catalyzed gas phase partial oxidations may either be below 1 bar, be 1 bar or be above 1 bar. In general, it is from 1 to 10 bar, usually from 1 to 3 bar.

The target conversion is effected during the residence time of the reaction gas mixture in the catalyst charge through which it is passed.

Owing to the generally marked exothermic character of the usually heterogeneously catalyzed gas phase partial oxidations of organic compounds with molecular oxygen, the reaction partners are typically diluted with a gas which is substantially inert under the conditions of the catalytic partial oxidation in the gas phase and is capable of absorbing heat of reaction released with its heat capacity.

One of the most frequently used inert diluent gases is molecular nitrogen which is used automatically when the oxygen source used for the heterogeneously catalyzed gas phase partial oxidation is air.

Owing to its general availability, another inert diluent gas which is used in many cases is steam. Both nitrogen and steam are additionally, in an advantageous manner, uncombustible inert diluent gases.

In many cases, cycle gas is also used as an inert diluent gas (cf., for example, EP-A 1180508). Cycle gas refers to the residual gas which remains after a one-stage or multistage (in the multistage heterogeneously catalyzed gas phase partial oxidation of organic compounds, the gas phase partial oxidation, in contrast to the one-stage heterogeneously catalyzed gas phase partial oxidation, is carried out not in one, but rather in at least two, reactors connected in series (which can merge into one another seamlessly in a common casing), in which case oxidant can be supplemented between successive reactors; multiple stages are employed especially when the partial oxidation proceeds in successive steps; in these cases, it is frequently appropriate to optimize both the catalyst and the other reaction conditions to the particular reaction step and to carry out the reaction step in a dedicated reactor, in a separate reaction stage; however, it can also be employed if, for reasons of heat removal or for other reasons (cf., for example, DE-A 19902562), the conversion is spread over a plurality of reactors connected in series; an example of a heterogeneously catalyzed gas phase partial oxidation which is frequently carried out in two stages is the partial oxidation of propylene to acrylic acid; in the first reaction stage, the propylene is oxidized to acrolein and, in the second reaction stage, the acrolein to acrylic acid; correspondingly, the preparation of methacrylic acid is usually carried out in two stages starting from isobutene; however, when suitable catalyst charges are used, both aforementioned partial oxidations can also be carried out in one stage (both steps in one reactor) heterogeneously catalyzed gas phase partial oxidation of at least one organic compound when the target product is removed more or less selectively (for example by absorption into a suitable solvent) from the product gas mixture. In general, it consists predominantly of the inert diluent gases used for the partial oxidation, and also of steam typically by-produced in the partial oxidation or added as a diluent gas and carbon oxides formed by undesired complete oxidation. In some cases, it also contains small amounts of oxygen which has not been consumed in the partial oxidation (residual oxygen) and/or unconverted organic starting compounds.

The steam formed as a by-product ensures in most cases that the partial oxidation proceeds without significant changes in volume of the reaction gas mixture.

According to the above, the inert diluent gas used in most heterogeneously catalyzed gas phase partial oxidations of organic compounds consists of $\geq 90\%$ by volume, frequently of $\geq 95\%$ by volume, of $N_2$, $H_2O$ and/or $CO_2$, and thus substantially of uncombustible inert diluent gases.

The inert diluent gases used are firstly helpful in taking up the heat of reaction and secondly ensure safe operation of the heterogeneously catalyzed gas phase partial oxidation of an organic compound by keeping the reaction gas mixture outside the explosion range. In heterogeneously catalyzed gas phase partial oxidations of unsaturated organic compounds, it is frequently also possible to use saturated hydrocarbons, i.e. combustible gases, as inert diluent gases.

It is also known that heterogeneously catalyzed gas phase partial oxidations of at least one organic compound over catalyst beds disposed in at least one oxidation reactor can be operated substantially continuously over prolonged periods over one and the same catalyst beds. The reaction conditions may generally be kept substantially constant.

However, the catalyst bed loses quality in the course of the operating time. In general, the activity in particular of the at least one catalyst bed deteriorates. This is disadvantageous in particular because the reactant conversion is thus reduced with increasing operating time of the at least one catalyst bed under otherwise constant operating conditions, which reduces the possible space-time yield.

EP-A 990 636 and EP-A 11 06 598 attempt to take into account the aforementioned development in the long-term operation of a heterogeneously catalyzed gas phase partial oxidation of at least one organic compound over one and the same catalyst bed by gradually increasing the temperature of the catalyst bed in the course of the operating time under otherwise substantially constant operating conditions, in order to substantially retain the partial conversion on single pass of the reaction gas mixture through the at least one catalyst bed.

A disadvantage of the procedure recommended in EP-A 99 636 and in EP-A 11 06 598 is that, with increasing increase in the temperature of the catalyst bed, its aging process is generally accelerated, which is why the catalyst bed is typically fully exchanged on attainment of the maximum value of the temperature of the catalyst bed.

EP-A 614 872 and DE-A 10 35 0822 recommend delaying the necessity of the full catalyst exchange by regenerating the catalyst bed from time to time (for example conducting a hot mixture of molecular oxygen and inert gas through the catalyst bed from time to time). However, a disadvantage of this procedure is that it entails an interruption in the production over a prolonged period.

DE-A 10 23 2748 recommends, as a compromise solution, instead of fully exchanging the catalyst bed, only replacing a portion thereof with a fresh catalyst charge.

A disadvantage of this proposal is that a partial change of the catalyst bed is also associated with significant cost and inconvenience.

As an approach to a solution, it has also already been proposed in principle to provide a more extensive catalyst bed I accommodated, in a comparatively costly and inconvenient manner, in an isothermal reactor and a smaller catalyst bed II accommodated, in a comparatively less costly and inconvenient manner, in an adiabatic reactor, with the aim that the adiabatic reactor begins to provide assistance where the isothermal reactor by itself no longer achieves the highest conversion, in order thus to delay to a maximum the exchange of the catalyst bed in the isothermal reactor.

However, a disadvantage of this procedure is that it requires an increased number of reactors and thus increased investment.

DETAILED DESCRIPTION OF THE INVENTION

Figure 1:
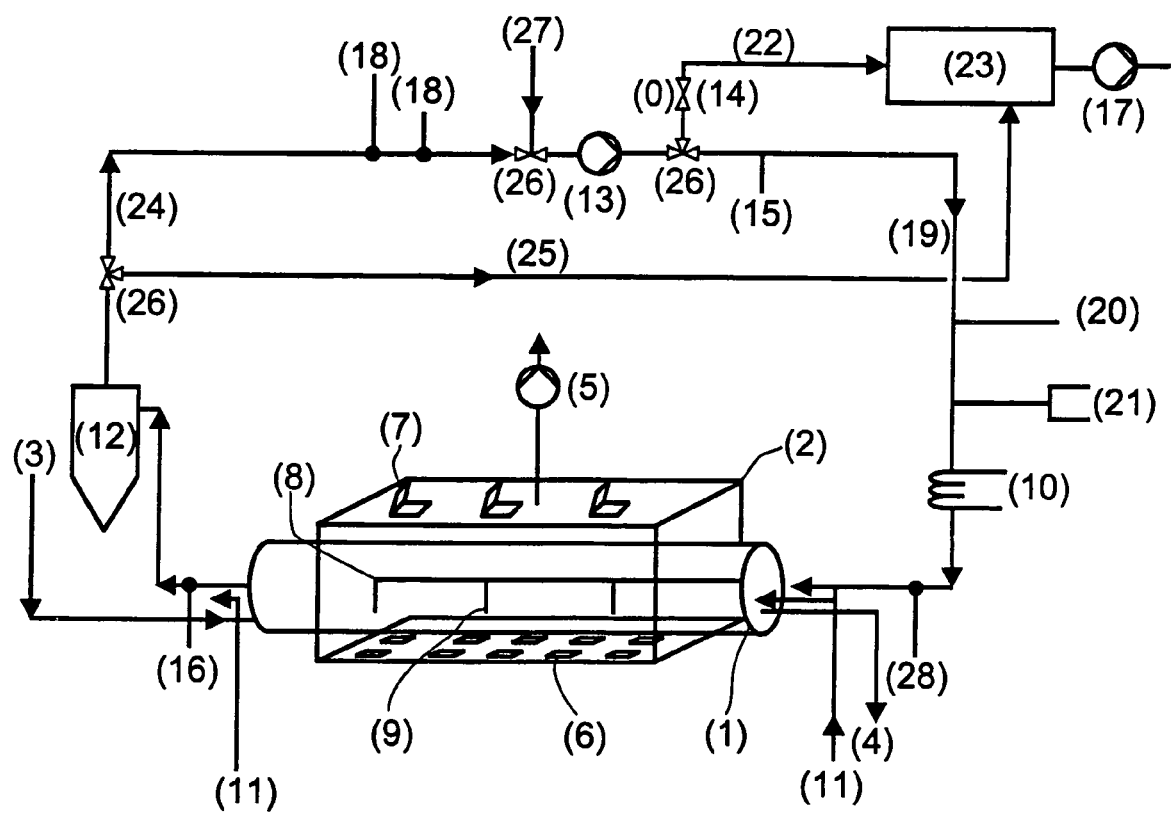
FIG. 1 is a schematic diagram of a rotary tube furnace used for calcinations.

In view of the prior art described, it is an object of the present invention to provide an improved process for the long-term operation of a heterogeneously catalyzed gas phase partial oxidation of at least one organic compound in at least one oxidation reactor and over at least one (one and the same) catalyst bed.

Accordingly, a process has been found for the long-term operation of a heterogeneously catalyzed gas phase partial oxidation of at least one organic compound in at least one oxidation reactor, in which a starting reaction gas mixture comprising the at least one organic compound, molecular oxygen and at least one inert diluent gas is passed through at least one catalyst bed at elevated temperature, which comprises, in order to counteract the deactivation of the at least one catalyst bed, increasing the working pressure in the gas phase, based on an identical hourly space velocity on the at least one catalyst bed of starting reaction gas mixture in $l$ (STP)/$l$·h, during the operating time of the catalyst bed.

Pressure increases which are a result of deposition in solid form in the fixed catalyst bed of components present in the reaction gas mixture in the course of the operating time are excluded.

The hourly space velocity on a catalyst bed catalyzing a reaction step of (starting) reaction gas mixture refers to the amount of (starting) reaction gas mixture in standard liters (=$l$ (STP); the volume in liters that the appropriate amount of (starting) reaction gas mixture would take up under standard conditions, i.e. at 25° C. and 1 bar) which is conducted per hour through one liter of catalyst bed. The hourly space velocity may also be based only on one constituent of the (starting) reaction gas mixture. In that case, it is the amount of this constituent in $l$ (STP)/$l$·h which is conducted per hour through one liter of the catalyst bed.

The realization of the inventive increase in the working pressure in the gas phase is possible, for example, in a simple manner by mounting a pressure regulator (an apparatus for regulating the working pressure in the at least one oxidation reactor) downstream (i.e. connected downstream of the at least one oxidation reactor) of the (outlet for the reaction gas mixture of the) at least one oxidation reactor containing the at least one catalyst bed. This may be, for example, a vane regulator or, in a particularly simple manner, a throttle apparatus, for example a throttle valve. Alternatively, it is also possible, for example, to insert only partially permeable perforated diaphragms into the flow path of the reaction gas mixture, in order thus to automatically increase the pressure drop of the reaction gas mixture on its flow path and thus, at the same hourly space velocity on the at least one catalyst bed of starting reaction gas mixture, the working pressure. Such a perforated diaphragm may have, for example, a plurality of passages (holes in the simplest case) which may successively be partly or fully closed.

The pressure regulating unit does not necessarily have to be mounted directly downstream of the relevant oxidation reactor. Rather, it is sufficient to realize the inventive procedure when the pressure regulating apparatus is introduced into the further flow path of the product gas mixture leaving the oxidation reactor in question and the pressure increase is propagated into the oxidation reaction as a result of back pressure. In other words, when the product gas mixture leaving the oxidation reactor is subsequently conducted into the lower region of a column for absorbing the target product in an absorption liquid introduced, for example, in the upper region of the column, the pressure regulator may also be disposed at the top of the absorption column. However, this variant will generally be less preferred, since column pressures are typically comparatively restricted for safety reasons. The absorption behavior might also be adversely affected. The same applies to the case in which the product gas mixture, on its further path, is conducted into the lower region of a column for fractional condensation of the target product. In general, the aforementioned columns comprise separating internals to increase the mass transfer surface area.

In the case of a series connection of oxidation reactors, a pressure regulating apparatus may be mounted downstream of each of the individual reactors in the context of the present invention.

The success of the inventive procedure can presumably be attributed to the pressure increase being accompanied by an increase in the residence time of the reactants over the catalyst surface. This increased residence time is then presumably sufficient in order to again enable the target reaction over reaction sites which have already been deactivated to a certain extent. In addition, the inventive measure is also accompanied by increased partial pressures of the relevant reactants.

The magnitude of the increase in the working pressure which is selected in the individual case in the process according to the invention depends both upon the extent of the deactivation of the catalyst bed at the time at which the working pressure is increased and upon the specific reaction system. Typically in accordance with the invention, the increase in the working pressure (in this document, always based for reasons of standardization on the entry point of the reaction gas mixture into the catalyst bed, which is calculated in this context to include inert preliminary beds) will be at least 25 bar or at least 50 bar before the catalyst bed is partly or fully exchanged. In general, the aforementioned increase in the working pressure in the process according to the invention will be from 25 or 50 mbar to 3000 mbar, frequently from 100 mbar to 2500 mbar, in many cases from 200 to 2000 mbar, often from 300 to 1500 mbar, sometimes from 400 to 1000 mbar and not rarely from 500 to 750 mbar.

Advantageously in accordance with the invention, the inventive pressure increase will be undertaken continuously and as a function of the deactivation rate of the at least one catalyst bed (a measure of the activity is the temperature which is required in order to achieve, at the same hourly space velocity on the catalyst bed and the same working pressure, the same reactant conversion based on single pass of the reaction gas mixture through the catalyst bed). However, it may also be undertaken in stages.

The highest value of the inventive increase in the working pressure is generally achieved when a further increase in the working pressure is accompanied by a significant reduction in the selectivity of target product formation. The latter may occur, for example, when excessively long residence times of the reactants over the sites on the catalyst surface which are still fully active lead to increasing full combustion, which reduces the yield of target product. However, such a reduction in selectivity can also be accepted with willingness, for example, if the demanded conversions would still be achievable only at temperatures which would damage, for example, the catalyst and/or the reactor.

This influence on the selectivity is normally also the reason why the heterogeneously catalyzed gas phase partial oxidation of at least one organic compound on the catalyst bed is not carried out at the greatest possible working pressure from the start. Ultimately, increased working pressures also cause increased starting reaction gas mixture compression costs. Another restriction for the inventive pressure increase may be the resulting difference between the highest and the lowest temperature in the catalyst bed, since in many partial oxidations this difference should frequently be ≦100° C., preferably ≦80° C. or ≦60° C. or ≦40° C., or ≦20° C., or ≦10C.

Frequently, the working pressures at the start of the process according to the invention will be from 1.2 to 2 bar. At the time at which the catalyst bed is exchanged, the working pressure will accordingly, in accordance with the invention, typically be up to 3 bar.

In principle, the process according to the invention is suitable for all heterogeneously catalyzed gas phase partial oxidations listed specifically at the outset of this document. These include in particular the heterogeneously catalyzed gas phase partial oxidation of propane to acrylic acid described in the documents WO 01/96270, DE-A 10316465, DE-A 10245585, DE-A 10246119. The aforementioned documents should be regarded as an integral part of this document.

However, the inventive procedure is particularly suitable for the heterogeneously catalyzed fixed bed gas phase partial oxidation, carried out preferably in a tube bundle reactor in one stage, of propene to acrolein and/or acrylic acid, and for the first and second stage of a heterogeneously catalyzed fixed bed gas phase partial oxidation, carried out in tube bundle reactors in two stages, of propene to acrolein or of acrolein to acrylic acid, as described, for example, in the documents EP-A 700 893, EP-A 700 714, DE-A 19 91 0508, DE-A 19 91 9596, DE-A 10351269, DE-A 10350812, DE-A 10350822, EP-A 11 59 247, DE-A 10 31 3208, DE-A 102004021764, DE-A 19 94 8248, EP-A 990 636, EP-A 11 06 598, DE-A 30 02 8289 and DE-A 10232482.

The process according to the invention is suitable for a heterogeneously catalyzed gas phase fixed bed partial oxidation of propene to acrolein especially when the catalysts used are those whose active composition is a multielement oxide which comprises the elements molybdenum and/or tungsten, and also at least one of the elements bismuth, tellurium, antimony, tin and copper, or is a multimetal oxide comprising the elements Mo, Bi and Fe. Multimetal oxide compositions of the aforementioned type which comprise Mo, Bi and Fe and are particularly suitable in accordance with the invention are in particular the multimetal oxide compositions comprising Mo, Bi and Fe which are disclosed in DE-A 10 34 4149 and in DE-A 10 34 4264. These are in particular also the multimetal oxide active compositions of the general formula I of DE-A 19 95 5176, the multimetal oxide active compositions of the general formula I of DE-A 19 94 8523, the multimetal oxide active compositions of the general formulae I, II and III of DE-A 10 10 1695, the multimetal oxide active compositions of the general formulae I, II and III of DE-A 19 94 8248 and the multimetal oxide active compositions of the general formulae I, II and III of DE-A 19955168 and also the multimetal oxide active compositions specified in EP-A 700714.

An application of the process according to the invention is also suitable when the catalysts used for the at least one fixed catalyst bed to be used in accordance with the invention, in the case of the partial oxidation of propene to acrolein, are the multimetal oxide catalysts comprising Mo, Bi and Fe which are disclosed in the documents DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4438217, DE-A 19855913, WO 98/24746, DE-A 19746210 (those of the general formula 11), JP-A 91/294239, EP-A 293224 and EP-A 700714. This applies in particular to the exemplary embodiments in these documents, and among these particular preference is given to those of EP-A 15565, EP-A 575897, DE-A 19746210 and DE-A 19855913. Particular emphasis is given in this context to a catalyst according to example 1c from EP-A 15565 and also to a catalyst to be prepared in a corresponding manner but whose active composition has the composition $Mo_{12}Ni_{6.5}Zn_2Fe_2Bi_1P_{0.0065}K_{0.06}Ox\cdot 10$ $SiO_2$. Emphasis is also given to the example having the serial number 3 from DE-A 19855913 (stoichiometry: $Mo_{12}Co_7Fe_3Bi_{0.6}K_{0.08}Si_{1.6}Ox$) as an unsupported hollow cylinder catalyst of geometry 5 mm×3 mm×2 mm or 5 mm×2 mm×2 mm (each external diameter×height×internal diameter) and also to the unsupported multimetal oxide II catalyst according to example 1 of DE-A 19746210. Mention should also be made of the multimetal oxide catalysts of U.S. Pat. No. 4438217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable in the context of the present invention are the multimetal oxide catalysts and geometries of DE-A 10101695 or WO 02/062737.

Also very suitable in the context of the present invention are example 1 of DE-A 10046957 (stoichiometry: $[Bi_2W_2O_9 \times 2WO_3]_{0.5}\cdot[Mo_{12}Co_{5.6}Fe_{2.94}Si_{1.59}K_{0.88}O_x]_1$) as an unsupported hollow cylinder (ring) catalyst of geometry 5 mm x 3 mm×2 mm or 5 mm×2 mm×2 mm (each external diameter× length×internal diameter), and also the coated catalysts 1, 2 and 3 of DE-A 10063162 (stoichiometry: $Mo_{12}Bi_{1.0}Fe_3Co_7Si_{1.6}K_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multitude of multimetal oxide active compositions particularly suitable for the catalysts of a propene partial oxidation to acrolein in the context of the present invention can be encompassed by the general formula I $$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions I can be intimately mixed in dry or in wet form. When they are mixed in dry form, the starting compounds are advantageously used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures from the spray tower of from 100 to 150° C.

Typically, the multimetal oxide active compositions of the general formula I are used in the fixed catalyst bed not in powder form, but rather shaped into certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter can be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined may also be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is advantageously moistened and dried again after application, for example by means of hot air. The coating thickness of the powder composition applied to the support body is advantageously selected within the range from 10 to 1000 µm, preferably within the range from 50 to 500 µm and more preferably within the range from 150 to 250 µm. Alternatively, the powder composition to be applied may also be applied to the support bodies directly from a suspension or solution thereof (for example in water).

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention in the first reaction stage is based. The support bodies can have a regular or irregular shape, although preference is given to regularly shaped support bodies having distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm (e.g. 8 mm) and whose external diameter is from 4 to 10 mm (e.g. 6 mm). In the case of rings suitable as support bodies according to the invention, the wall thickness is also typically from 1 to 4 mm. According to the invention, annular support bodies to be used preferably have a length of from 2 to 6 mm, an external diameter of from 4 to 8 mm and a wall thickness of from 1 to 2 mm. Suitable as support bodies according to the invention are in particular rings of the geometry 7 mm×3 mm×4 mm or 5mm×3 mm×2 mm (external diameter×length×internal diameter). It will be appreciated that the fineness of the catalytically active oxide compositions to be applied to the surface of the support body will be adapted to the desired coating thickness (cf. EP-A 714 700).

Multimetal oxide active compositions which are particularly suitable for the catalysts of the fixed catalyst bed of a propene partial oxidation to acrolein in the context of the present invention are also compositions of the general formula II

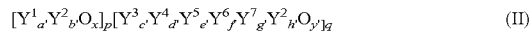  (II)

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x', y'=numbers which are determined by the valency and frequency of the elements in II other than oxygen and
p, q=numbers whose p/q ratio is from 0.1 to 10, comprising three-dimensional regions of the chemical composition $Y^1_{a'}Y^2_{b'}O_{x'}$ which are delimited from their local environment as a consequence of their different chemical composition from their local environment, and whose maximum diameter (longest line passing through the center of the region and connecting two points on the surface (interface)) is from 1 nm to 100 µm, frequently from 10 nm to 500 nm or from 1 µm to 50 or 25 µm.

Particularly advantageous multimetal oxide compositions 11 are those in which $Y^1$ is only bismuth.

Among these, preference is given in turn to those of the general formula III $$[Bi_{a''}Z^2_{b''}O_{x''}]_{p''}[Z^2_{12}Z^3_{c''}Z^4_{d''}Fe_{e''}Z^{f''}Z^6_{g''}Z^7_{h''}O_{y''}]_q \qquad (III)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x", y"=numbers which are determined by the valency and frequency of the elements in IIII other than oxygen,
p", q"=numbers whose p"/q" ratio is from 0.1 to 5, preferably from 0.5 to 2, and very particular preference is given to those compositions III in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_{a'}Y^2_{b'}O_{x'}]_p$ ($[Bi_{a''}Z^2_{bg''}O_{x''}]_{p''}$) of the multimetal oxide compositions II (multimetal oxide compositions III) suitable in accordance with the invention in the multimetal oxide compositions II (multimetal oxide compositions III) suitable in accordance with the invention are in the form of three-dimensional regions of the chemical composition $Y^1_{a''}Y^2_{b''}Op_{x''}[Bi_{a''}Z^2_{b''}O_{x''}]$ which are delimited from their local environment as a consequence of their different chemical composition from their local environment, and whose maximum diameter is in the range from 1 nm to 100 µm.

With regard to the shaping, the statements made for the multimetal oxide I catalysts apply to the multimetal oxide II catalysts.

The preparation of multimetal oxide active compositions 11 is described, for example, in EP-A 575897 and also in DE-A 19855913, DE-A 10344149 and DE-A 10344264.

Suitable active compositions for catalysts of at least one fixed catalyst bed suitable for the partial oxidation of acrolein to acrylic acid in the context of the present invention are the multimetal oxides known for this reaction type which comprise the elements Mo and V.

Such multimetal oxide active compositions comprising Mo and V can be taken, for example, from U.S. Pat. No. 3775474, U.S. Pat. No. 3954855, U.S. Pat. No. 3893951, and U.S. Pat. No. 4339355, or EP-A 614872 or EP-A 1041062, or WO 03/055835, or WO 03/077653.

Especially suitable are also the multimetal oxide active compositions of DE-A 10 32 5487 and also of DE-A 10 32 5488.

Also particularly suitable as active compositions for the fixed bed catalysts for the partial oxidation of acrolein to acrylic acid in the context of the present invention are the multimetal oxide compositions of EP-A 427508, DE-A 29 09 671, DE-C 31 51 805, DE-B 26 26 887, DE-A 43 02 991, EP-A 700 893, EP-A 7147 00 and DE-A 19 73 6105. Particular preference is given in this context to the exemplary embodiments of EP-A 714 700 and of DE-A 19 73 6105.

A multitude of these multimetal oxide active compositions comprising the elements Mo and V can be encompassed by the general formula IV $$Mo_{12}V_aX^1_bX^2_cX^3_dX^4_eX^5_fX^6_gO_n \qquad (IV)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in IV other than oxygen.

Preferred embodiments among the active multimetal oxides IV in the context of the present invention are those which are encompassed by the following definitions of the variables of the general formula IV:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in IV other than oxygen.

However, multimetal oxides IV which are very particularly preferred according to the invention are those of the general formula V $$Mo_{12}V_{a''}Y^1_{b''}Y^2_{c''}Y^5_{f''}Y^6_{g''}O_{n''} \qquad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in V other than oxygen.

Multimetal oxide active compositions (IV) are obtainable in a manner known per se, for example disclosed in DE-A 4335973 or in EP-A 714700. In particular, suitable multimetal oxide active compositions comprising Mo and V in the context of the present invention for the partial oxidation of acrolein to acrylic acid are also the multimetal oxide active compositions of DE-A 10 261 186.

In principle, such multimetal oxide active compositions comprising Mo and V, especially those of the general formula IV, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to intimate mixing in wet form. This is typically done by mixing the starting compounds in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions comprising Mo and V, especially those of the general formula IV, may be used for the process according to the invention of a partial oxidation of acrolein to acrylic acid either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2909671, EP-A 293859 or by EP-A 714700.

To coat the support bodies, the powder composition to be applied is appropriately moistened and is dried again after application, for example by means of hot air. The coating thickness of the powder composition applied to the support body is advantageously selected within the range from 10 to 1000 μm, preferably within the range from 50 to 500 μm and more preferably in the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders. It is suitable to use substantially nonporous, surface-roughened, spherical supports made of steatite whose diameter is from 1 to 10 mm (e.g. 8 mm), preferably from 4 to 5 mm. However, suitable support bodies also include cylinders whose length is from 2 to 10 mm and whose external diameter is from 4 to 10 mm. In the case of rings which are suitable in accordance with the invention as support bodies, the wall thickness is also typically from 1 to 4 mm. Annular support bodies to be used with preference in accordance with the invention have a length of from 3 to 6 mm, an external diameter of from 4 to 8 mm and a wall thickness of from 1 to 2 mm. Suitable support bodies according to the invention are also in particular rings of geometry 7 mm×3 mm×4 mm (external diameter×length×internal diameter). It will be appreciated that the fineness of the catalytically active oxide compositions to be applied to the surface of the support body is adapted to the desired coating thickness (cf. EP-A 714 700).

Advantageous multimetal oxide active compositions comprising Mo and V and which are to be used in the context of the present invention for an acrolein partial oxidation to acrylic acid are also compositions of the general formula VI

$$[D]_p[E]_q \quad (VI)$$

in which the variables are each defined as follows:

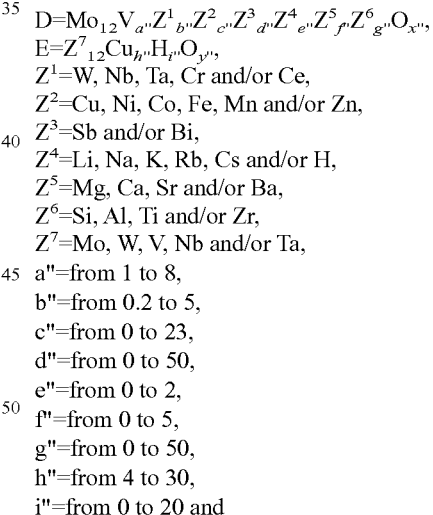

$D=Mo_{12}V_{a''}Z^1_{b''}Z^2_{c''}Z^3_{d''}Z^4_{e''}Z^5_{f''}Z^6_{g''}O_{x''}$,
$E=Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements other than oxygen in VI and
p,q=numbers other than zero whose p/q ratio is from 160:1 to 1:1, and which are obtainable by separately preforming a multimetal oxide composition E

$$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1, Z^2, Z^3, Z^4, Z^5, Z6$ which comprises the abovementioned elements in the stoichiometry D $$Mo_{12}V_{a''}Z^1_{b''}Z^2_{c''}Z^3_{b''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to those multimetal oxide active compositions VI in which the preformed solid starting composition 1 is incorporated into an aqueous starting composition 2 at a temperature of <70° C. A detailed description of the preparation of multimetal oxide composition III catalysts is contained, for example, in EP-A 668104, DE-A 19736105 and DE-A 19528646.

With regard to the shaping, the statements made for the multimetal oxide active composition IV catalysts apply to the multimetal oxide active composition VI catalysts.

Further multimetal oxide active compositions comprising Mo and V which are advantageous in the context described are also multielement oxide active compositions of the general formula VII $$[A]_p[B]_q[C]_r \quad (VII)$$

in which the variables are each defined as follows:
$A = Mo_{12}V_aX^1_bX^2_cX^3_dX^4_eX^5_fX^6_gO_x$,
$B = X^7_1Cu_hH_iO_y$,
$C = X^8_1Sb_jH_kO_z$,
$X^1$=W, Nb, Ta, Cr and/or Ce, preferably W, Nb and/or Cr,
$X^2$=Cu, Ni, Co, Fe, Mn and/or Zn, preferably Cu, Ni, Co and/or Fe,
$X^3$=Sb and/or Bi, preferably Sb,
$X^4$=Li, Na, K, Rb, Cs and/or H, preferably Na and/or K,
$X^5$=Mg, Ca, Sr and/or Ba, preferably Ca, Sr and/or Ba,
$X^6$=Si, Al, Ti and/or Zr, preferably Si, Al and/or Ti,
$X^7$=Mo, W, V, Nb and/or Ta, preferably Mo and/or W,
$X^8$=Cu, Ni, Zn, Co, Fe, Cd, Mn, Mg, Ca, Sr and/or Ba, preferably Cu and/or Zn, more preferably Cu,
b=from 0.2 to 5, preferably from 0.5 to 2.5
c=from 0 to 23, preferably from 0 to 4,
d=from 0 to 50, preferably from 0 to 3,
e=from 0 to 2, preferably from 0 to 0.3,
f=from 0 to 5, preferably from 0 to 2,
g=from 0 to 50, preferably from 0 to 20,
h=from 0.3 to 2.5, preferably from 0.5 to 2, more preferably from 0.75 to 1.5,
i=from 0 to 2, preferably from 0 to 1,
j=from 0.1 to 50, preferably from 0.2 to 20, more preferably from 0.2 to 5,
k=from 0 to 50, preferably from 0 to 20, more preferably from 0 to 12,
x,y,z=numbers which are determined by the valency and frequency of the elements in A, B, C other than oxygen,
p,q=positive numbers
r=0 or a positive number, preferably a positive number, where the p/(q+r) ratio =from 20:1 to 1:20, preferably from 5:1 to 1:14 and more preferably from 2:1 to 1:8 and, in the case that r is a positive number, the q/r ratio =from 20:1 to 1:20, preferably from 4:1 to 1:4, more preferably from 2:1 to 1:2 and most preferably 1:1, which contain the fraction [A]p in the form of three-dimensional regions (phases) A of the chemical composition A: $Mo_{12}VaX^1_bX^2_cX^3_dX^4_eX^5_fX^5_gO_x$, the fraction $[B]_q$ in the form of three-dimensional regions (phases) B of the chemical composition
B: $X_1^7CU_hH_iO_y$, and the fraction $[C]_r$ in the form of three-dimensional regions (phases) C of the chemical composition
C: $X_1^8Sb_jH_kO_z$, where the regions A, B and, where present, C are distributed relative to each other as in a mixture of finely divided A, finely divided B and, where present, finely divided C, and where all variables are to be selected within the predefined ranges with the proviso that the molar fraction of the element Mo in the total amount of all elements in the multielement oxide active composition VII other than oxygen is from 20 mol % to 80 mol %, the molar ratio of Mo present in the catalytically active multielement oxide composition VII to V present in the catalytically active multielement oxide composition VII, MoN, is from 15:1 to 1:1, the corresponding molar Mo/Cu ratio is from 30:1 to 1:3 and the corresponding molar Mo/(total amount of W and Nb) ratio is from 80:1 to 1:4.

In the context of the present invention, preferred multielement oxide active compositions VII are those whose regions A have a composition within the following stoichiometric pattern of the general formula Vil:

$$MO_{12}V_aX^1_bX^2_cX^5_fX^6_gO_x \quad (VIII)$$

where
$X^1$=W and/or Nb,
$X^2$=Cu and/or Ni,
$X^5$=Ca and/or Sr,
$X^6$=Si and/or Al,
a=from 2 to 6,
b=from 1 to 2,
c=from 1 to 3,
f=from 0 to 0.75,
g=from 0 to 10, and
x=a number which is determined by the valency and frequency of the elements in (VIII) other than oxygen.

The term "phase" used in connection with the multielement oxide active compositions VIII means three-dimensional regions whose chemical composition is different to that of their environment. The phases are not necessarily x-ray-homogeneous. In general, phase A forms a continuous phase in which particles of phase B and, where present, C are dispersed.

The finely divided phases B and, where present, C advantageously consist of particles whose largest diameter, i.e. longest line passing through the center of the particles and connecting two points on the surface of the particles, is up to 300 μm, preferably from 0.1 to 200 μm, more preferably from 0.5 to 50 μm and most preferably from 1 to 30 μm. However, particles having a longest diameter of from 10 to 80 μm or from 75 to 125 μm are also suitable.

In principle, the phases A, B and, where present, C may be in amorphous and/or crystalline form in the multielement oxide active compositions VII.

The intimate dry mixtures on which the multielement oxide active compositions of the general formula VII are based and which are subsequently to be treated thermally to convert them to active compositions may be obtained, for example, as described in the documents WO 02/24327, DE-A 4405514, DE-A 4440891, DE-A 19528646, DE-A 19740493, EP-A 756894, DE-A 19815280, DE-A 19815278, EP-A 774297, DE-A 19815281, EP-A 668104 and DE-A 19736105.

The basic principle of preparing intimate dry mixtures whose thermal treatment leads to multielement oxide active compositions of the general formula VII is to preform, in finely divided form, separately or combined together, at least one multielement oxide composition B ($X_1^7Cu_hH_iO_y$) as the starting composition 1 and, where appropriate, one or more multielement oxide compositions C ($X_1^8S_{bj}H_kO_z$) as the starting composition 2, and subsequently to intimately contact, in the desired ratio (corresponding to the general formula VII), the starting compositions 1 and, where appropriate, 2 with a mixture which comprises sources of the elemental constituents of the multielement oxide composition A

$$MO_{12}V_aX_b^1X_c^2X_d^3X_e^4X_f^5X_g^6O_x \qquad (A)$$

in a composition corresponding to the stoichiometry A, and optionally to dry the resulting intimate mixture.

The intimate contacting of the constituents of the starting compositions 1 and, where appropriate, 2 with the mixture comprising the sources of the elemental constituents of the multimetal oxide composition A (starting composition 3) may be effected either in dry or in wet form. In the latter case, care has to be taken merely that the preformed phases (crystallites) B and, where appropriate, C do not go into solution. In an aqueous medium, the latter is usually ensured at pH values which do not deviate too far from 7 and at temperatures which are not excessively high. When the intimate contacting is effected in wet form, there is normally final drying to give the intimate dry mixture to be thermally treated in accordance with the invention (for example by spray-drying). In the case of dry mixing, such a dry mass is obtained automatically. It will be appreciated that the phases B and, where appropriate, C preformed in finely divided form may also be incorporated into a plastically reshapeable mixture which comprises the sources of the elemental constituents of the multimetal oxide composition A, as recommended by DE-A 10046928. The intimate contacting of the constituents of the starting compositions 1 and, where appropriate, 2 with the sources of the multielement oxide composition A (starting composition 3) may of course also be effected as described in DE-A 19815281.

The thermal treatment to obtain the active composition and the shaping may be effected as described for the multimetal oxide active compositions IV to VI.

Quite generally, multimetal oxide active composition IV to VII catalysts may advantageously be prepared in accordance with the teaching of DE-A 10 325 487 or DE-A 10 325 488.

The performance of the reaction stage (and the application of the process according to the invention) from propene to acrolein can be carried out with the catalysts described as suitable for the fixed catalyst bed in question, in the simplest manner and appropriately from an application point of view, in a tube bundle reactor charged with the fixed bed catalysts, as described, for example, in EP-A 700 714 or DE-A 4 431 949 or WO 03/057653, or WO 03/055835, or WO 03/059857, or WO 03/076373.

In other words, in the simplest manner, the fixed catalyst bed is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor is generally from 250 to 450° C., frequently from 300 to 400° C. or from 300 to 380° C. The associated reaction temperatures also then move within these temperature ranges. Suitable heat exchange media are in particular fluid heating media. It is particularly appropriate to use melts of salts such as potassium nitrate, potassium nitrite, sodium nitrite and/or sodium nitrate, or of low-melting metals such as sodium, mercury and also alloys of different metals. Ionic liquids can also be used.

Appropriately, the starting reaction gas mixture is fed to the charge of fixed bed catalyst preheated to the desired reaction temperature.

Especially in the case of desired high (e.g. $\geq 130$ l (STP)/l·h, or $\geq 140$ l (STP)/l·h, or $\geq 150$ l (STP)/l·h, or $\geq 160$ l (STP)/l·h, but generally $\leq 600$ l (STP)/l·h, frequently $\leq 350$ l (STP)/l·h) hourly space velocities of propene on the fixed catalyst bed, the propene partial oxidation process is appropriately carried out in a two- or multizone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3147084, DE-A 2201528, EP-A 383224 and DE-A 2903582 are also suitable. Another process description is given by EP-A 1106598.

In other words, in a simple manner, the at least one fixed catalyst bed to be used in accordance with the invention is then disposed in the uniformly charged metal tubes of a tube bundle reactor and two substantially spatially separated heating media, generally salt melts, are conducted around the metal tubes. The tube section over which the particular salt bath extends represents a reaction zone.

For example, a salt bath A preferably flows around that section of the tubes (the reaction zone A) in which the oxidative conversion of propene (in single pass) proceeds until a conversion value in the range from 40 to 80 mol % is achieved and a salt bath B preferably flows around the section of the tubes (the reaction zone B) in which the subsequent oxidative conversion of propene (in single pass) proceeds until a conversion value of generally at least 93 mol % is achieved (if required, reaction zones A, B may be followed by further reaction zones which are kept at individual temperatures).

Within the particular temperature zone, the salt bath may in principle be conducted as in the one-zone method. The inlet temperature of the salt bath B is normally from at least 5 to 10° C. above the temperature of the salt bath A. Otherwise, the inlet temperatures may be within the temperature range for the inlet temperature recommended for the one-zone method.

Otherwise, the two-zone high-load method for the propene partial oxidation to acrolein may be carried out as described, for example, in DE-A 10 30 8836, EP-A 11 06 598, or as described in WO 01/36364, or DE-A 19 92 7624, or DE-A 19 94 8523, DE-A 10 31 3210, DE-A 10 31 3213 or as described in DE-A 19 94 8248.

Generally, the process according to the invention in a propene partial oxidation to acrolein is suitable for propene hourly space velocities on the fixed catalyst bed of $\leq 70$ l (STP)/l·h, or $\geq 70$ l (STP)/l·h, $\geq 90$ l (STP)/l·h, $\geq 110$ l (STP)/l·h, $\geq 130$ l (STP)/l·h, $\geq 140$ l (STP)/l·h, $\geq 160$ l (STP)/l·h, $\geq 180$ l (STP)/l·h, $\geq 240$ l (STP)/l·h, $\geq 300$ l (STP)/l·h, but normally $\leq 600$ l (STP)/l·h. Here, the hourly space velocity is based on the volume of the fixed catalyst bed excluding any sections used which consist exclusively of inert material (as is generally the case in this document, unless explicitly stated otherwise).

To prepare the fixed catalyst bed for an inventive partial oxidation of propene to acrolein, it is possible to use in the process according to the invention only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation of propene to acrolein (and consist of inert material) (shaped diluent bodies). Useful materials for such inert shaped bodies are in principle all of those which are also suitable as support materials for "propene-to-acrolein" coated catalysts. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. According to the invention, the inert shaped diluent bodies selected will preferably be those whose geometry corresponds to that of the first-stage shaped catalyst bodies to be diluted by them.

In general, it is favorable when the chemical composition of the active composition used for the described propene partial oxidation to acrolein does not change over the fixed catalyst bed. In other words, although the active composition used for an individual shaped catalyst body may be a mixture of different multimetal oxides comprising, for example, the elements Mo and/or W and also at least one of the elements Bi, Fe, Sb, Sn and Cu, the same mixture is then advantageously used for all shaped catalyst bodies of the fixed catalyst bed.

In the propene partial oxidation to acrolein, the volume-specific (i.e. normalized to the unit of volume) activity preferably normally increases continuously, abruptly or in stages within the fixed catalyst bed in the flow direction of the starting reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, or catalyst activity, in a certain volume of the fixed bed.

A volume-specific activity increasing at least once in the flow direction of the reaction gas mixture over the fixed catalyst bed can thus be attained in a simple manner, for example, by beginning the bed with a high fraction of inert shaped diluent bodies based on one type of shaped catalyst bodies, and then reducing this fraction of shaped diluent bodies in the flow direction either continuously or, at least once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having the higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activities may also be used for the fixed catalyst bed of an inventive propene partial oxidation to acrolein. These mixtures may in turn be diluted with inert diluent bodies.

Upstream and/or downstream of the sections, having active composition, of the fixed catalyst bed of an inventive propene partial oxidation to acrolein may be disposed beds consisting exclusively of inert material (for example only shaped diluent bodies). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4-5 mm.

In many cases, the section of the fixed catalyst bed having active composition is structured as follows for a propene partial oxidation to acrolein in the flow direction of the reaction gas mixture in the process according to the invention.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total lengths of the section of the fixed bed catalyst charge having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, preferably from 10 to 40% by weight or from 20 to 40% by weight and more preferably from 25 to 35% by weight. Downstream of this first zone is then frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies diluted only to a lesser extent (than in the first zone), or, most preferably, a sole bed of the same shaped catalyst bodies which have also been used in the first zone.

The aforementioned is especially true when the shaped catalyst bodies used in the fixed catalyst bed are unsupported catalyst rings or coated catalyst rings (especially those which are listed in this document as preferred). For the purposes of the aforementioned structuring, both the shaped catalyst bodies or their support rings and the shaped diluent bodies in the process according to the invention advantageously have substantially the ring geometry 5 mm×3 mm×2 mm (external diameter×length ×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 1 or 5 to 20% generally begins the fixed catalyst bed in the flow direction of the reaction gas mixture. It is normally used as a heating zone for the reaction gas mixture.

Typically, the catalyst tubes in the tube bundle reactors for the stage of partial oxidation of propene to acrolein are manufactured from ferritic steel and typically have a wall thickness of from 1 to 3 mm. Their internal diameter is generally (uniformly) from 20 to 30 mm, frequently from 21 to 26 mm. Appropriately from an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 are usually exceptional for this reaction stage. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

The performance of the reaction stage (and the application of the process according to the invention) from acrolein to acrylic acid may be carried out with the catalysts described as suitable for the fixed catalyst bed of this reaction, in the simplest manner and appropriately from an application point of view, in a tube bundle reactor charged with the fixed bed catalysts, as described, for example, in EP-A 700 893 or DE-A 4 431 949 or WO 03/057653, or WO 03/055835, or WO 03/059857, or WO 03/076373.

In other words, in the simplest manner, the fixed catalyst bed to be used is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor (in this document, this corresponds to the temperature of the fixed catalyst bed) is generally from 220 to 350° C., frequently from 245 to 285° C. or from 245 to 265° C. Suitable heat exchange media are in particular fluid heating media. It is particularly appropriate to use melts of salts such as potassium nitrate, potassium nitrite, sodium nitrite and/or sodium nitrate, or of low-melting metals such as sodium, mercury and also alloys of different metals. Ionic liquids can also be used.

Appropriately, the starting reaction gas mixture is fed to the charge of fixed bed catalyst preheated to the desired reaction temperature.

Especially in the case of desired high (e.g. $\geq$130 l (STP)/l·h, or $\geq$140 l (STP)/l·h, but generally $\leq$350 l (STP)/l·h, or $\leq$600 l (STP)/l·h) hourly space velocities of acrolein on the fixed catalyst bed, the process according to the invention for the acrolein partial oxidation to acrylic acid is appropriately carried out in a two- or multizone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3147084, DE-A 2201528, EP-A 383224 and DE-A 2903582 are also suitable.

In other words, in the simplest manner, the at least one fixed catalyst bed to be used in accordance with the invention is disposed in the uniformly charged metal tubes of a tube bundle reactor and two substantially spatially separated heating media, generally salt melts, are conducted around the metal tubes. The tube section over which the particular salt bath extends represents a temperature or reaction zone.

For example, a salt bath C preferably flows around that section of the tubes (the reaction zone C) in which the oxidative conversion of acrolein (in single pass) proceeds until a conversion value in the range from 55 to 85 mol % is achieved and a salt bath D preferably flows around the section of the tubes (the reaction zone D) in which the subsequent oxidative conversion of acrolein (in single pass) proceeds until a conversion value of generally at least 90 mol % is achieved (if required, reaction zones C, D may be followed by further reaction zones which are kept at individual temperatures).

Within the particular temperature zone, the salt bath may in principle be conducted as in the one-zone method. The inlet temperature of the salt bath D is normally from at least 5 to 10° C. above the temperature of the salt bath C. Otherwise, the inlet temperatures may be within the temperature range for the inlet temperature recommended for the one-zone method.

Otherwise, the two-zone high-load method of acrolein partial oxidation to acrylic acid may be carried out as described, for example, in DE-A 19 94 8523, EP-A 11 06 598 or as described in DE-A 19 94 8248.

Accordingly, the process according to the invention is suitable for acrolein hourly space velocities on the fixed catalyst bed of $\leq$70 l (STP)/l·h, or $\geq$70 l (STP)/l·h, $\geq$90 l (STP)/l·h, $\geq$110 l (STP)/l·h, $\geq$130 l (STP)/l·h, $\geq$180 l (STP)/l·h, $\geq$240 l (STP)/l·h, $\geq$300 l (STP)/l·h, but normally $\leq$600 l (STP)/l·h. The hourly space velocity is based on the volume of the fixed catalyst bed excluding any sections used which consist exclusively of inert material.

To prepare the at least one fixed catalyst bed, it is possible to use, for an inventive partial oxidation of acrolein to acrylic acid, only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation (and consist of inert material) (shaped diluent bodies). Useful materials for such inert shaped bodies are in principle all of those which are also suitable as support materials for coated catalysts "acrolein-to-acrylic acid" which are suitable in accordance with the invention. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. According to the invention, the inert shaped diluent bodies selected will preferably be those whose geometry corresponds to that of the shaped catalyst bodies to be diluted by them.

In general, it is favorable in the context of an inventive partial oxidation of acrolein to acrylic acid when the chemical composition of the active composition used does not change over the fixed catalyst bed. In other words, although the active composition used for an individual shaped catalyst body may be a mixture of different multimetal oxides comprising the elements Mo and V, the same mixture then advantageously has to be used for all shaped catalyst bodies of the fixed catalyst bed.

For an inventive partial oxidation of acrolein to acrylic acid, the volume-specific (i.e. normalized to the unit of volume) activity preferably normally increases continuously, abruptly or in stages within the fixed catalyst bed in the flow direction of the reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, i.e. catalyst activity, in a certain volume of the fixed bed.

A volume-specific activity increasing at least once in the flow direction of the reaction gas mixture over the fixed catalyst bed can thus be attained in a simple manner for a process for acrolein partial oxidation to acrylic acid according to the invention, for example, by beginning the bed with a high fraction of inert shaped diluent bodies based on one type of shaped catalyst bodies, and then reducing this fraction of shaped diluent bodies in the flow direction either continuously or, at least once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having the higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activities may also be used for the fixed catalyst bed of an inventive acrolein partial oxidation to acrylic acid. These mixtures may in turn be diluted with inert diluent bodies.

Upstream and/or downstream of the sections of the fixed catalyst bed having active composition may be disposed beds consisting exclusively of inert material (for example only shaped diluent bodies). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4-5 mm.

In many cases, in an inventive process for acrolein partial oxidation to acrylic acid, the section of the fixed catalyst bed having active composition is structured as follows in the flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total lengths of the section of the fixed bed catalyst charge having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone is then frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies diluted only to a lesser extent (than in the first zone or in the first two zones), or, most preferably, a sole bed of the same shaped catalyst bodies which have also been used in the first zone (or in the first two zones).

The aforementioned is especially true when the shaped catalyst bodies used in the fixed catalyst bed are coated catalyst rings or coated catalyst spheres (especially those which are listed in this document as preferred for an acrolein partial oxidation to acrylic acid). For the purposes of the aforementioned structuring, both the shaped catalyst bodies or their support rings and the shaped diluent bodies in a process for acrolein partial oxidation to acrylic acid according to the invention advantageously have substantially the ring geometry 7 mm×3 mm×4 mm (external diameter×length×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 5 to 20% generally begins the fixed catalyst bed for acrolein partial oxidation in the flow direction of the reaction gas mixture. It is normally used as a heating zone for the reaction gas mixture.

Typically, the catalyst tubes in the tube bundle reactors for the inventive acrolein partial oxidation are manufactured from ferritic steel and typically have a wall thickness of from 1 to 3 mm. Their internal diameter is generally (uniformly) from 20 to 30 mm, frequently from 21 to 26 mm. Appropriately from an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 are usually exceptional for the acrolein partial oxidation. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

As already described, both the propene and the acrolein partial oxidation in the process according to the invention may be carried out in one-zone or in two-zone tube bundle reactors. When the two reaction stages are connected in series, it is also possible for only the first reaction stage to be carried out in a one-zone tube bundle reactor and the second reaction stage in a two-zone tube bundle reactor (or vice versa). In this case, the product gas mixture of the first reaction stage is, if appropriate after supplementation with inert gas or with molecular oxygen or with inert gas and molecular oxygen, and also if appropriate on completion of direct and/or indirect intermediate cooling, fed directly to the second reaction stage.

Between the tube bundle reactors of the first and the second reaction stage may be disposed an intermediate cooler which may optionally contain inert beds.

It will be appreciated that the fixed catalyst bed of the propene partial oxidation and the fixed catalyst bed of the acrolein partial oxidation for the inventive process of a two-stage partial oxidation of propene to acrylic acid may also be accommodated spatially successively in a single multiple-catalyst-tube tube bundle reactor likewise having, for example, two temperature zones, as described, for example, by WO 03/059857, EP-A 911313 and EP-A 990636. This case is referred to as a single-reactor two-stage process. In this case, one temperature zone generally extends over one fixed catalyst bed. Between the two fixed catalyst beds may additionally be disposed an inert bed which is, if appropriate, disposed in a third temperature zone and is heated separately. The catalyst tubes may be continuous or interrupted by the inert bed.

The inert gas to be used for the charge gas mixture of the "propene-to-acrolein reaction stage" (the starting reaction gas mixture 1) may, irrespective of the propene hourly space velocity selected for the fixed catalyst bed (and irrespective of whether there is a downstream "acrolein-to-acrylic acid reaction stage"), consist, for example, of $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

However, the inert diluent gas may also consist, for example, of from 2 to 35 or 20% by weight of $H_2O$ and from 65 to 98% by volume of $N_2$.

However, at propene hourly space velocities on the fixed catalyst bed of the "propene-to-acrolein reaction stage" of above 250 l (STP)/l·h, the use is recommended for the process according to the invention of inert diluent gases such as propane, ethane, methane, butane, pentane, $CO_2$, CO, steam and/or noble gases. However, it will be appreciated that these gases may also be used at lower propene hourly space velocities.

The working pressure in the course of the inventive gas phase partial oxidation of the propene to acrolein (especially at the start of the operating time of a fixed catalyst bed) may be either below atmospheric pressure (for example up to 0.5 bar) or above atmospheric pressure. Typically, the working pressure in the gas phase partial oxidation of propene will be at values of from 1 to 5 bar, frequently from 1 to 3 bar.

Normally, the reaction pressure in the inventive propene partial oxidation to acrolein will not exceed 100 bar. However, it is essential to the invention that the working pressure during the operating time of the at least one fixed catalyst bed for the partial oxidation of propene to acrolein, based on an identical hourly space velocity thereon of starting: reaction gas mixture 1 in I (STP)/I·h, is increased, in order to counteract the deactivation of the at least one fixed catalyst bed. The pressure may be increased to the extent described in the general section of this document. It will be appreciated that the/this inventive procedure may be employed quite generally in combination with the procedures for prolonging the on-stream time of a catalyst bed recommended in the documents EP-A 990 636, EP-A 11 06 598, EP-A 614 872, DE-A 10 35 0822, DE-A 10 23 2748 and DE-A 10351269. It is thus possible to achieve catalyst bed on-stream times of several years. The molar $O_2$:propene ratio in the starting reaction gas mixture 1 for the propene partial oxidation to acrolein which is conducted through the appropriate fixed catalyst bed in the process according to the invention will normally be $\geq 1$ (substantially irrespective of whether there is a downstream acrolein partial oxidation stage to acrylic acid). Typically, this ratio will be at values of $\leq 3$. Frequently, the molar $O_2$:propene ratio in the aforementioned charge gas mixture will advantageously be from 1:2 to 1:1.5. In many cases, the process for the propene partial oxidation to acrolein will be performed at a propene:oxygen:inert gas (including steam) volume ratio (I (STP)/I·h) in the starting reaction gas mixture 1 of 1 :(1 to 3):(3 to 30), preferably of 1:(1.5 to 2.3):(1 0

The propene fraction in the starting reaction gas mixture 1 may lie, for example, at values of from 4 to 20% by volume, frequently from 5 or 7 to 15% by volume or from 6 or 8 to 12% by volume or from 5 to 8% by volume (based in each case on the total volume).

A typical composition of the starting reaction gas mixture 1 (irrespective of the hourly space velocity selected and irrespective of whether an acrolein partial oxidation to acrylic acid follows) may comprise the following components:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.025 to 0.04% by volume of acrolein,
from 10.4 to 10.7% by volume of $O_2$ and,
as the remainder ad 100%, molecular nitrogen, or: 5.4% by volume of propene,
10.5% by volume of oxygen,
1.2% by volume of $CO_x$,
80.5% by volume of $N_2$ and
2.4% by volume of $H_2O$.

However, the starting reaction gas mixture 1 for the propene partial oxidation to acrolein may, in accordance with the invention, also have the following composition:

from 6 to 15% by volume of propene,
from 4 to 30% by volume (frequently from 6 to 15% by volume) of water,
from $\geq 0$ to 10% by volume (preferably from $\geq 0$ to 5% by volume) of constituents other than propene, water, oxygen and nitrogen, sufficient molecular oxygen that the molar ratio of molecular oxygen present to molecular propene present is from 1.5 to 2.5, and, as the remainder up to 100% by volume of the total amount, molecular nitrogen.

Another possible starting reaction gas mixture 1 composition for the propene partial oxidation to acrolein may, in accordance with the invention, comprise:

6.0% by volume of propene,
60% by volume of air and
34% by volume of $H_2O$.

Alternatively, starting reaction gas mixtures 1 of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used for the "propene-to-acrolein reaction stage".

Further starting reaction gas mixtures 1 for the "propene-to-acrolein reaction stage" which are suitable in accordance with the invention may lie within the following composition framework:

from 7 to 11% by volume of propene,
from 6 to 12% by volume of water,
from $\geq 0$ to 5% by volume of constituents other than propene, water, oxygen and nitrogen, $\geq$ sufficient molecular oxygen that the molar ratio of oxygen present to molecular propene present is from 1.4 to 2.2, and, as the remainder up to 100% by volume of the total amount, molecular nitrogen.

The propene to be used in the starting reaction gas mixture 1 is in particular polymer-grade propene and chemical-grade propene, as described, for example, by DE-A 10232748.

It should also be mentioned at this point that, irrespective of whether an "acrolein-to-acrylic acid reaction stage" follows, a portion of the charge gas mixture of the "propene-to-acrolein reaction stage" may be what is known as cycle gas. As already described, this is gas which remains after the product removal, in the work-up (acrolein and acrylic acid removal) which customarily follows the last reaction stage, from the product gas mixture of this reaction stage and is generally recycled partly as a substantially inert diluent gas to charge the propene reaction stage and/or any subsequent acrolein reaction stage.

The oxygen source used is normally air.

The hourly space velocity on the fixed catalyst bed (excluding pure inert sections) of starting reaction gas mixture 1 in the process according to the invention will typically be from 1000 to 10 000 l (STP)/l·h, usually from 1000 to 5000 l (STP)/l·h, frequently from 1500 to 4000 l (STP)/l·h (irrespective of whether an "acrolein-to-acrylic acid reaction stage" follows).

When the propene partial oxidation to acrolein is followed by an acrolein partial oxidation, the product gas mixture of the propene reaction stage is, if appropriate after intermediate cooling, fed to the acrolein reaction stage. The oxygen required in the acrolein reaction stage may already have been added to the starting reaction gas mixture 1 for the propene reaction stage as an excess and thus be a constituent of the product gas mixture of the propene reaction stage. In this case, the product gas mixture of the propene reaction stage, intermediately cooled if appropriate, may directly be the charge gas mixture of the acrolein reaction stage. However, some or all of the oxygen required for the second oxidation step from acrolein to acrylic acid may also not be added to the product gas mixture of the propene reaction stage until it enters the acrolein reaction stage, for example in the form of air. This addition may be associated with direct cooling of the product gas mixture of the acrolein reaction stage.

Resulting from the aforementioned connection, the inert gas present in the charge gas mixture for an acrolein reaction stage (the starting reaction gas mixture 2) (irrespective of whether there is a preceding propene reaction stage) may consist of, for example, $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

However, the inert diluent gas in the charge gas for the acrolein reaction stage will frequently consist of from 5 to 25 or 20% by weight of $H_2O$ (may be formed, for example, in a preceding propene reaction stage and/or added if appropriate) and of from 70 to 90% by volume of $N_2$.

However, at acrolein hourly space velocities on the fixed catalyst bed for the partial oxidation of acrolein to acrylic acid of above 250 l (STP)/l·h, the use of inert diluent gases such as propane, ethane, methane, butane, pentane, $CO_2$, steam and/or noble gases is recommended for the process according to the invention. It will be appreciated that these gases may also be used even at relatively low acrolein hourly space velocities.

The working pressure in the inventive gas phase partial oxidation of acrolein to acrylic acid (especially at the start of the operating time of a fixed catalyst bed) may be either below atmospheric pressure (for example up to 0.5 bar) or above atmospheric pressure. Typically, the working pressure in the gas phase partial oxidation of acrolein will be at values of from 1 to 5 bar, frequently from 1 to 3 bar.

Normally, the reaction pressure in the inventive acrolein partial oxidation will not exceed 100 bar. However, it is essential to the invention that the working pressure during the operating time of the at least one fixed catalyst bed for the partial oxidation of acrolein to acrylic acid, based on an identical hourly space velocity thereon of starting reaction gas mixture 2 in l (STP)/l·l, is increased, in order to counteract the deactivation of the at least one fixed catalyst bed. The pressure may be increased to the extent described in the general section of this document. It will be appreciated that the/this inventive procedure may be employed quite generally in combination with the procedures for prolonging the on-stream time of a catalyst bed recommended in the documents EP-A 990 636, EP-A 11 06 598, EP-A 614 872, DE-A 10 35 0822, DE-A 10 23 2748 and DE-A 10351269. It is thus possible to achieve catalyst bed on-stream times of several years.

The molar $O_2$:acrolein ratio in the charge gas mixture for an acrolein reaction stage which is conducted through the appropriate fixed catalyst bed in the process according to the invention (irrespective of whether there is a preceding propene reaction stage or not) will normally be $\geq 1$. Typically, this ratio will be at values of $\geq 3$. According to the invention, the molar $O_2$:acrolein ratio in the aforementioned charge gas mixture will frequently be from 1 to 2 or from 1 to 1.5. In many cases, the process according to the invention will be performed at an acrolein:oxygen:steam:inert gas volume ratio (l (STP)) of 1 :(1 to 3):(0 to 20):(3 to 30), preferably of 1 :(1 to 3):(0.5 to 10reaction gas mixture 2 (charge gas mixture for the acrolein reaction stage).

The acrolein fraction in the charge gas mixture for the acrolein reaction stage may be, for example., (irrespective of whether there is a preceding propene reaction stage or not) at values of from 3 or 6 to 15% by volume, frequently from 4 or 6 to 10% by volume, or from 5 to 8% by volume (based in each case on the total volume). The hourly space velocity on the fixed catalyst bed (here excluding pure inert sections) of charge gas mixture (starting reaction gas mixture 2) in an inventive "acrolein-to-acrylic acid process" will typically be, as for the "propene-to-acrolein reaction stage", from 1000 to 10 000 l (STP)/l·h, usually from 1000 to 5000 l (STP)/l·h, frequently from 1500 to 4000 l (STP)/l·h.

When the process according to the invention is performed, a fresh fixed catalyst bed for the partial oxidation of propene to acrolein, after it has been conditioned, will normally (i.e. irrespective of whether a partial oxidation of the acrolein formed to acrylic acid follows) be operated in such a way that, after determining the composition of the starting reaction gas mixture 1 and determining the hourly space velocity on the fixed catalyst bed for the propene partial oxidation of starting reaction gas mixture 1, the temperature of the fixed catalyst bed (or the inlet temperature of the heating medium into the heating zone of the tube bundle reactor) is adjusted in such a way that the conversion $C^{pro}$ of propene on single pass of the reaction gas mixture 1 through the fixed catalyst bed is at least 93 mol %. When favorable catalysts are used, values of $C^{pro}$ of $\geq$94 mol %, or $\geq$95 mol %, or $\geq$96 mol %, or $\geq$97 mol % and frequently even more are also possible.

When the heterogeneously catalyzed partial oxidation of propene to acrolein is performed continuously, the composition of the starting reaction gas mixture 1 and the hourly space velocity on the fixed catalyst bed of starting reaction gas mixture 1 will be kept substantially constant (if desired, the hourly space velocity is adapted to the fluctuating market demand). A fall in the activity of the fixed catalyst bed over time will normally be counteracted under these production conditions by increasing the temperature of the fixed catalyst bed (the inlet temperature of the heating medium into the temperature zone of the tube bundle reactor) from time to time (the flow rate of the heating medium is normally likewise kept substantially constant), in order to keep the propene conversion in single pass of the reaction gas mixture within the desired target corridor (i.e. at $C^{pro}$ of $\geq$93 mol %, or $\geq$94 mol %, or $\geq$95 mol %, or $\geq$96 mol %, or $\geq$97 mol %). However, such a procedure above is associated with the disadvantages described at the outset of this document.

The procedure is therefore advantageously to interrupt the gas phase partial oxidation from time to time in accordance with the invention, in order to conduct a gas mixture G consisting of molecular oxygen, inert gas and, if appropriate, steam through the fixed catalyst bed at a temperature of the fixed catalyst bed of from 250 to 550° C. as described in DE-A 10351269. Subsequently, the partial oxidation of propene is continued while substantially retaining the process conditions (the propene hourly space velocity on the fixed catalyst bed is preferably restored slowly) and the temperature of the fixed catalyst bed is adjusted in such a way that the propene conversion attains the desired target value. In general, this temperature value, for the same conversion, will be at a somewhat lower value than the temperature that the fixed catalyst bed had before the interruption of the partial oxidation and the inventive treatment with the gas mixture G. Starting from this temperature value of the fixed catalyst bed, the partial oxidation is continued while substantially retaining the remaining conditions, and the fall in the activity of the fixed catalyst bed over time will appropriately in turn be counteracted by increasing the temperature of the fixed catalyst bed from time to time. Within, for example, one successive calendar year, the partial oxidation, appropriately in accordance with the invention, is in turn interrupted at least once, in order to conduct the gas mixture G through the fixed catalyst bed in the inventive manner. Afterward, the partial oxidation, advantageously in accordance with the invention, is started up again as described, etc. However, the inventive measure of increasing the working pressure will appropriately be allowed to exert its influence together with increasing temperature of the catalyst bed over the operating time of the catalyst bed. This can be effected in stages or uniformly.

In a corresponding manner, when performing the process according to the invention, a fresh fixed catalyst bed for the partial oxidation of acrolein to acrylic acid, after it has been conditioned, will normally be operated in such a way that, after determining the operation of this reaction stage and the composition of the starting reaction gas mixture 2 and determining the hourly space velocity on the appropriate fixed catalyst bed of starting reaction gas mixture 2, the temperature of the fixed catalyst bed (or the inlet temperature of the heating medium into the heating zone of the tube bundle reactor) is adjusted in such a way that the conversion $C^{acr}$ of acrolein in single pass of the starting reaction gas mixture 2 through the fixed catalyst bed is at least 90 mol %. When favorable catalysts are used, values for $C^{acr}$ of $\geq$92 mol %, or $\geq$94 mol %, or $\geq$96 mol %, or $\geq$98 mol %, and frequently even $\geq$99 mol % and more are also possible.

When the heterogeneously catalyzed partial oxidation of acrolein to acrylic acid is performed continuously, the composition of the starting reaction gas mixture 2 and the hourly space velocity on the fixed catalyst bed of starting reaction gas mixture 2 will be kept substantially constant (if appropriate the hourly space velocity is adapted to the fluctuating market demand). A fall in the activity of the fixed catalyst bed over time will normally be counteracted under these production conditions by increasing the temperature of the fixed catalyst bed (the inlet temperature of the heating medium into the temperature zone of the tube bundle reactor) from time to time (the flow rate of the heating medium is likewise normally substantially retained), in order to keep the acrolein conversion in single pass of the charge gas mixture within the desired target corridor (i.e. at values of $\geq$90 mol %, or $\geq$92 mol %, or $\geq$94 mol %, or $\geq$96 mol %, or $\geq$98 mol %, or $\geq$99 mol %). However, such a procedure alone is associated with the disadvantages described at the outset of this document.

The procedure will therefore, advantageously, be to interrupt the gas phase partial oxidation at least once, for example before the undertaken temperature increase of the fixed catalyst bed is permanently $\geq$10° C. or $\geq$8° C. (based on the temperature of the fixed catalyst bed set beforehand), in order to conduct the gas mixture G through the fixed catalyst bed of the partial oxidation of acrolein to acrylic acid (in a two-stage partial oxidation of propene to acrylic acid, conducting it via the fixed catalyst bed of the propene oxidation of acrolein) at a temperature of the fixed catalyst bed of from 200 to 450° C. Subsequently, the partial oxidation is continued while substantially retaining the process conditions (the acrolein hourly space velocity on the appropriate fixed catalyst bed is preferably restored slowly, as described, for example, in DE-A 10337788) and the temperature of the fixed catalyst bed is adjusted in such a way that the acrolein conversion attains the desired target value. In general, this temperature value, for the same conversion, will be at a somewhat lower value than the temperature that the fixed catalyst bed had before the interruption of the partial oxidation and the inventive treatment with the gas mixture G. Starting from this temperature value of the fixed catalyst bed, the partial oxidation of the acrolein is continued while substantially retaining the remaining conditions, and the fall in the activity of the fixed catalyst bed over time is appropriately in turn counteracted by increasing the temperature of the fixed catalyst bed from time to time. For example, before the temperature increase of the fixed catalyst bed which has been carried out is permanently $\geq$10° C. or $\geq$8° C., the partial oxidation is, in accordance with the invention, in turn interrupted at least once, in order to conduct the gas mixture G through the fixed catalyst bed of the acrolein partial oxidation of acrolein to acrylic acid (if appropriate conducting it via the fixed catalyst bed of a propene reaction stage). Afterward, the partial oxidation, advantageously in accordance with the invention, is started up again as described, etc. However, the inventive measure of increasing the working pressure will appropriately be allowed to exert its influence together with increasing temperature of the catalyst bed over the operating time of the catalyst bed. This can be effected in stages or uniformly. In the case of a two-stage inventive partial oxidation of propene to acrylic acid, it is possible, for example, for a pressure regulating apparatus to be mounted downstream of each of the two reaction stages and additionally at the top of a downstream absorption or fractionating condensation column which has the purpose of transferring the acrylic acid from the gaseous product gas mixture of the partial oxidation conducted in the lower section thereof into the condensed phase.

However, in the case of such a two-stage reaction, a pressure regulating apparatus downstream of (preferably immediately at the outlet of the product gas mixture) the second reaction stage, in which acrolein is partially oxidized to acrylic acid, is frequently sufficient.

It is surprising that, in the case of a fixed catalyst bed partially deactivated over prolonged operating times, the measure of increasing the working pressures brings about a reactivation of the catalyst bed. It is also surprising that, when this pressure increase is undertaken judiciously, it is not associated with any significant reduction in the selectivity of target product formation.

The process according to the invention thus enables on the one hand longer on-stream times of the catalyst beds, especially fixed catalyst beds, in the reactor systems before they have to be partly or fully exchanged. On the other hand, the reactant conversions achieved, integrated over time, are likewise increased.

The process according to the invention is especially advantageous when, in the case of a propene partial oxidation to acrolein (in the case of an acrolein partial oxidation to acrylic acid), it is operated at an hourly space velocity on the fixed catalyst bed of propene (of acrolein) of $\geq 110$ l (STP)/l·h, or $\geq 120$ l (STP)/l·h, or $\geq 130$ l (STP)/l·h (under higher reactant hourly space velocities, catalysts generally deactivate more rapidly). In the case of a two-stage partial oxidation of propene to acrylic acid connected in series, the hourly space velocity on the fixed catalyst bed for the acrolein partial oxidation of acrolein may in each case be up to 20 l (STP)/l·h below the propene hourly space velocity on the fixed catalyst bed for the propene partial oxidation.

When the process according to the invention is combined with the procedure for the intermediate regeneration of the catalyst bed, it is possible to operate the catalyst bed at a predetermined conversion in long-term operation always below a set maximum temperature.

The removal of the acrylic acid from the product gas mixture and associated cycle gas formation may be effected as described in WO 97/48669.

Generally, freshly charged fixed catalyst beds for a propene partial oxidation and acrolein partial oxidation to acrolein and acrylic acid respectively will be configured in such a way that, as described in EP-A 990 636 and EP-A 11 06 598, both the hotspot formation and their temperature sensitivity are very low.

Finally, it should be emphasized that, in all gas phase partial oxidations addressed and discussed in this document, the inventive increase in the working pressure may be undertaken after 2000, or after 4000, or after 7000, or after 9000, or after 12 000, or after 15 000, or after 18 000, or after 21 000, or after 24 000, or after 27 000, or after 30 000 or more operating hours of the at least one catalyst bed. Intermediate regenerations are included therein. In a two-stage propene partial oxidation of propene to acrylic acid, it has been found to be advantageous, in the case of fresh catalyst beds, to begin the reaction operation with an inlet pressure into the propene reaction stage of from 1.4 to 1.9 bar, and to increase this inlet pressure to from 2.5 to 3.0 bar over the operating time.

It should also be emphasized that the performance of the process according to the invention normally requires at least one air compressor to compress the air typically used as an oxygen source (for example a radial compressor according to DE-A 10259023 and DE-A 10353014), in order to bring the starting reaction gas mixture to the working pressure required. Normally, the air compressors to be used for heterogeneously catalyzed partial gas phase oxidations are designed for economic reasons in such a way that, at a given hourly space velocity on the catalyst bed of starting reaction gas mixture, it is possible at best to pass through a working pressure range of up to 0.5 bar. Accordingly, to realize the inventive procedure, advantageous air compressors (for example the radial compressors mentioned) for the reaction gas mixture are designed in such a way that, at a given hourly space velocity on the catalyst bed of starting reaction gas mixture, they can pass through a working pressure range of from >0.5 to 4 bar, frequently from 0.6 to 3.5 bar, in many cases from 0.7 to 3 bar, and often from 0.8 to 2.5 bar or from 1 to 2 bar (i.e. the maximum possible working pressure by means of the compressor may be up to 4 bar above the minimum working pressure). The aforementioned is especially true when the hourly space velocity on the catalyst bed of starting reaction gas mixture is $\geq 1500$ l (STP)/l·h, or $\geq 2000$ l (STP)l·h, or $\geq 2500$ l (STP)/l·h, or $\geq 3000$ l (STP)/l·h, or $\geq 4000$ l (STP)/l·h. In general, the aforementioned hourly space velocity in the process according to the invention is at values of $\geq 5000$ l (STP)/l·h. Optionally, other constituents (for example cycle gas) of the starting reaction gas mixture may if required also be brought to working pressure in the air compressor. However, reactants such as propene and propane are usually stored as liquid and generally evaporated directly to working pressure therefrom. In some cases, cycle gas is compressed separately.

EXAMPLE AND COMPARATIVE EXAMPLES

A) Preparation of a catalyst $C_p$ to be used in the propene partial oxidation to acrolein Preparation of an annular supported catalyst having the following stoichiometry of the active multimetal oxide:

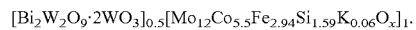

$[Bi_2W_2O_9 \cdot 2WO_3]_{0.5}[Mo_{12}Co_{5.5}Fe_{2.94}Si_{1.59}K_{0.06}O_x]_1$.

1. Preparation of a starting composition 1

209.3 kg of tungstic acid (72.94% by weight of W) were stirred in portions into 775 kg of an aqueous bismuth nitrate solution in nitric acid (11.2% by weight of Bi; free nitric acid from 3 to 5% by weight; mass density: from 1.22 to 1.27 g/ml) at 25° C. The resulting aqueous mixture was subsequently stirred at 25° C. for a further 2 h and subsequently spray-dried.

The spray-drying was effected in a rotating disk spray tower in countercurrent at a gas inlet temperature of 300±10° C. and a gas outlet temperature of 100±10° C. The resulting spray powder (particle size a substantially uniform 30 μm) which had an ignition loss of 12% by weight (ignite at 600° C. under air for 3 h) was subsequently converted to a paste in a kneader using 16.8% by weight (based on the powder) of water and extruded by means of an extruder (rotational moment: ≦50 Nm) to extrudates of diameter 6 mm. These were cut into sections of 6 cm, dried under air on a 3-zone belt dryer at a residence time of 120 min at temperatures of 90-95° C. (zone 1) and 125° C. (zone 2) and 125° C. (zone 3), and then thermally treated at a temperature in the range from 780 to 810° C. (calcined; in a rotary tube oven flowed through by air (capacity 1.54 m³, 200 m³ (STP) of air/h)). When precisely adjusting the calcination temperature, it is essential that it has to be directed to the desired phase composition of the cacination product. The desired phases are $WO_3$ (monoclinic) and $Bi_2W_2O_9$; the presence of $\gamma$-$Bi_2WO_6$ (Russellite) is undesired. Therefore, should the compound $\gamma$-$Bi_2WO_6$ still be detectable by a reflection in the x-ray powder diffractogram after the calcination at a reflection angle of $2\Theta=28.4°$ (CuKa radiation), the preparation has to be repeated and the calcination temperature increased within the temperature range specified or the residence time increased at constant calcination temperature, until the disappearance of the reflection is achieved. The preformed calcined mixed oxide obtained in this way was ground so that the $X_{50}$ value (cf. Ullmann's Encyclopedia of Industrial Chemistry, 6$^{th}$ Edition (1998) Electronic Release, Chapter 3.1.4 or DIN 66141) of the resulting particle size was 5 mm. The ground material was then mixed with 1% by weight (based on the ground material) of finely divided $SiO_2$ from Degussa of the Sipernat® type (bulk density 150 g/l; $X_{50}$ value of the $SiO_2$ particles was 10 μm, the BET surface area was 100 m2/g).

2. Preparation of a starting composition 2

A solution A was prepared by dissolving 213 kg of ammonium heptamolybdate tetrahydrate (81.5% by weight of $MoO_3$) at 60° C. with stirring in 600 l of water and the resulting solution was admixed while maintaining the 60° C. and stirring with 0.97 kg of an aqueous potassium hydroxide solution (46.8% by weight of KOH) at 20° C.

A solution B was prepared by introducing 116.25 kg of an aqueous iron (III) nitrate solution (14.2% by weight of Fe) at 60° C. into 262.9 kg of an aqueous cobalt (II) nitrate solution (12.4% by weight of Co). Subsequently, while maintaining the 60° C., solution B was continuously pumped into the initially charged solution A over a period of 30 minutes. Subsequently, the mixture was stirred at 60° C. for 15 minutes. 19.16 kg of a Ludox silica gel from Dupont (46.80% by weight of $SiO_2$, density: from 1.36 to 1.42 g/ml, pH from 8.5 to 9.5, max. alkali content 0.5% by weight) were then added to the resulting aqueous mixture, and the mixture was stirred afterward at 60° C. for a further 15 minutes.

Subsequently, the mixture was spray-dried in countercurrent in a rotating disk spray tower (gas inlet temperature: 400±10° C., gas outlet temperature: 140±5° C). The resulting spray powder had an ignition loss of approx. 30% by weight (ignite under air at 600° C. for 3 h) and a substantially uniform particle size of 30 μm.

Preparation of the multimetal oxide active composition

The starting composition 1 was mixed homogeneously with the starting composition 2 in the amounts required for a multimetal oxide active composition of the stoichiometry

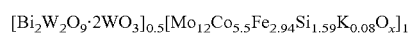

$[Bi_2W_2O_9 \cdot 2WO_3]_{0.5}[Mo_{12}Co_{5.5}Fe_{2.94}Si_{1.59}K_{0.08}O_x]_1$ in a mixer having bladed heads. Based on the aforementioned overall composition, an additional 1% by weight of finely divided graphite from Timcal AG (San Antonio, US) of the TIMREX P44 type (sieve analysis: min. 50% by weight<24 μm, max. 10% by weight>24 μm and<48 μm, max. 5% by weight >48 μm, BET surface area: from 6 to 13 m²/g) were mixed in homogeneously. The resulting mixture was then conveyed in a compactor (from Hosokawa Bepex GmbH, D-74211 Leingarten) of the K200/100 compactor pactor type having concave, fluted smooth rolls (gap width: 2.8 mm, sieve width: 1.0 mm, lower particle size sieve width: 400 μm, target compressive force: 60 kN, screw rotation rate: from 65 to 70 revolutions per minute). The resulting compactate had a hardness of 10 N and a substantially uniform particle size of from 400 μm to 1 mm.

The compactate was subsequently mixed with, based on its weight, a further 2% by weight of the same graphite and subsequently compressed in a Kilian rotary tableting press of the R×73 type from Kilian, D-50735 Cologne, under a nitrogen atmosphere to give annular shaped unsupported catalyst precursor bodies of geometry (external diameter×length×internal diameter) 5 mm×3 mm×2 mm and having a side crushing strength of 19 N ±3N.

In this document, side crushing strength refers to the crushing strength when the annular shaped unsupported catalyst precursor body is compressed at right angles to the cylinder surface (i.e. parallel to the surface of the ring orifice).

All side crushing strengths in this document relate to a determination by means of a material testing machine from Zwick GmbH & Co. (D-89079 Ulm) of the Z 2.5 / TS1S type. This material testing machine is designed for quasistatic stress having a single-impetus, stationary, dynamic or varying profile. It is suitable for tensile, compressive and bending tests. The installed force transducer of the KAF-TC type from A.S.T. (D-01 307 Dresden) having the manufacturer number 03-2038 was calibrated in accordance with DIN EN ISO 7500-1 and could be used for the 1-500 N measurement range (relative measurement uncertainty: ±0.2%).

The measurements were carried out with the following parameters:
Initial force: 0.5 N.
Rate of initial force: 10 mm/min.
Testing rate: 1.6 mm/min.

The upper die was initially lowered slowly down to just above the cylinder surface of the annular shaped unsupported catalyst precursor body. The upper die was then stopped, in order subsequently to be lowered at the distinctly slower testing rate with the minimum initial force required for further lowering.

The initial force at which the shaped unsupported catalyst precursor body exhibits crack formation is the side crushing strength (SCS).

For the final thermal treatment, in each case 1000 g of the shaped unsupported catalyst precursor bodies were heated in a muffle furnace flowed through by air (capacity 60 l, l/h of air per gram of shaped unsupported catalyst precursor body) initially from room temperature (25° C.) to 190° C. at a heating rate of 180° C./h. This temperature was maintained for 1 h and then increased to 21° C. at a heating rate of 60° C./h. The temperature of 210° C. was in turn maintained over 1 h before it was increased to 230° C. at a heating rate of 60° C./h. This temperature was likewise maintained for 1 h before it was increased to 265° C., again at a heating rate of 60° C./h. The temperature of 265° C. was subsequently likewise maintained over 1 h. Afterward, the furnace was initially cooled to room temperature and the decomposition phase thus substantially completed. The furnace was then heated to 465° C. at a heating rate of 180° C./h and this calcination temperature maintained over 4 h.

Annular unsupported catalysts $C_p$ were obtained from the annular shaped unsupported catalyst precursor bodies.

The specific surface area S, the total pore volume V, the pore diameter $d^{max}$ which makes the greatest contribution to the total pore volume, and the percentages of those pore diameters in the total pore volume whose diameter is >0.1 and ≧1 μm, for the resulting annular unsupported catalysts $C_p$ were as follows:

S=7.6 cm²/g.
V=0.27 cm3/g.
$d^{max}[\mu m]=0.6$.
$V^{0.1}_{1\_}\%=79$.

In addition, the ratio R of apparent mass density to true mass density p (as defined in EP-A 1340538) was 0.66.

On the industrial scale, the same annular catalyst was prepared by means of a belt calcining apparatus by thermal treatment as described in Example 1 of DE-A 10046957 (except that the bed height in the decomposition (chambers 1 to 4) was advantageously 44 mm at a residence time per chamber of 1.46 h and, in the calcination (chambers 5 to 8), it was advantageously 130 mm at a residence time of 4.67 h); the chambers had a surface area (at a uniform chamber length of 1.40 m) of 1.29 m² (decomposition) and 1.40 m² (calcination) and were flowed through from below through the coarse-mesh belt by 75 m³ (STP)/h of supply air which was aspirated by means of rotating ventilators. Within the chambers, the temporal and local deviation of the temperature from the target value was always >2° C. Otherwise, the procedure was as described in Example 1 of DE-A 10046957.

B) Preparation of a catalyst $C_A$ (coated catalyst) to be used in the acrolein partial oxidation to acrylic acid and having the stoichiometry $Mo_{12}V_3W_{1.2}Cu_{2.4}O_x$ of the active composition 1. General description of the rotary tube furnace used for calcination A schematic diagram of the rotary tube furnace is shown by the FIG. 1 appended to this document. The reference numerals which follow relate to this FIG. 1.

The central element of the rotary tube furnace is the rotary tube (1). It is 4000 mm long and has an internal diameter of 700 mm. It is manufactured from 1.4893 stainless steel and has a wall thickness of 10 mm.

On the interior wall of the rotary tube furnace are mounted lifting lances which have a height of 5 cm and a length of 23.5 cm. They primarily serve the purpose of lifting the material to be thermally treated in the rotary tube furnace, thus mixing it.

At one and the same height of the rotary tube furnace are mounted in each case four lifting lances (a quadruple) equidistantly around the circumference (separation in each case 90°). Along the rotary tube furnace are disposed eight such quadruples (each 23.5 cm apart). The lifting lances of two adjacent quadruples are offset relative to one another on the circumference. At the start and at the end of the rotary tube furnace (first and last 23.5 cm) there are no lifting lances.

The rotary tube rotates freely in a cuboid (2) which has four electrically heated (resistance heating) heating zones which are successive in the length of the rotary tube and are of equal length, each of which encloses the circumference of the rotary tube furnace. Each of the heating zones can heat the appropriate rotary tube section to temperatures between room temperature and 850° C. The maximum heating output of each heating zone is 30 kW. The distance between electrical heating zone and rotary tube exterior surface is about 10 cm. At the start and at the end, the rotary tube projects approx. 30 cm beyond the cuboid.

The rotation rate may be variably adjusted between 0 and 3 revolutions per minute. The rotary tube can be rotated either to the left or to the right. In the case of rotation to the right, the material remains in the rotary tube; in the case of rotation to the left, the material is conveyed from inlet (3) to outlet (4). The inclination angle of the rotary tube to the horizontal may be variably adjusted between 0° and 2°. In batchwise operation, it is in fact 0°. In continuous operation, the lowermost point of the rotary tube is at the material outlet. The rotary tube may be rapidly cooled by switching off the electrical heating zones and switching on a ventilator (5). This aspirates ambient air through holes (6) in the lower base of the cuboid, and conveys it through three flaps (7), having variably adjustable opening, in the lid.

The material inlet is controlled via a rotary star feeder (mass control). The material output is, as already mentioned, controlled via the rotation direction of the rotary tube.

In the case of batchwise operation of the rotary tube, an amount of material of from 250 to 500 kg may be thermally treated. The amount is normally disposed exclusively in the heated section of the rotary tube.

From a lance (8) lying on the central axis of the rotary tube, a total of three thermoelements (9) lead vertically into the material at intervals of 800 mm. They enable the determination of the temperature of the material. In this document, temperature of the material refers to the arithmetic mean of the three thermoelement temperatures. According to the invention, the maximum deviation of two measured temperatures within the material in the rotary tube is appropriately less than 30° C., preferably less than 20° C., more preferably less than 10° C. and most preferably less than 5 or 3° C.

Gas streams may be conducted through the rotary tube, by means of which the calcination atmosphere or generally the atmosphere of the thermal treatment of the material can be adjusted.

The heater (10) offers the possibility of heating the gas stream conducted into the rotary tube to the desired temperature before its entry into the rotary tube (for example to the temperature desired in the rotary tube for the material). The maximum output of the heater is 1×50 kW+1×30 kW. In principle, the heater (10) may be, for example, an indirect heat exchanger. Such a heater may in principle also be used as a cooler. However, it is generally an electrical heater in which the gas stream is conducted over metal wires heated using electricity (appropriately a 97D/80 CSN flow heater from C. Schniewindt KG, 58805 Neuerade, Germany).

In principle, the rotary tube apparatus provides the possibility of partly or fully recycling the gas stream conducted through the rotary tube. The recycle line required for this purpose is connected to the rotary tube in a mobile manner at the rotary tube inlet and at the rotary tube outlet using ball bearings or using graphite pressure seals. These connections are flushed with inert gas (e.g. nitrogen) (barrier gas). The two flush streams (11) supplement the gas stream conducted through the rotary tube at the inlet into the rotary tube and at the outlet from the rotary tube. Appropriately, the rotary tube narrows at its start and at its end and projects into the tube of the recycle line leading to and away from it respectively.

Downstream of the outlet of the gas stream conducted through the rotary tube is disposed a cyclone (12) to remove solid particles entrained with the gas stream (the centrifugal separator separates solid particles suspended in the gas phase by interaction of centrifugal force and gravity; the centrifugal force of the gas stream rotating as a spiral accelerates the sedimentation of the suspended particles).

The conveying of the cycle gas stream (24) (the gas circulation) is effected by means of a cycle gas compressor (13) (ventilator) which aspirates in the direction of the cyclone and forces in the other direction. Directly downstream of the cycle gas compressor, the gas pressure is generally above one atmosphere. Downstream of the cycle gas compressor is disposed a cycle gas outlet (cycle gas may be discharged via a regulating valve (14)). A diaphragm disposed downstream of the outlet (cross-sectional reduction by about a factor of 3, pressure reducer) (15) eases the discharge.

The pressure downstream of the rotary tube outlet can be controlled via the regulating valve. This is effected in combination with a pressure sensor (16) mounted downstream of the rotary tube outlet, the offgas compressor (17) (ventilator) which aspirates toward the regulating valve, the cycle gas compressor (13) and the fresh gas feed. Relative to the external pressure, the pressure (directly) downstream of the rotary tube outlet may be set, for example, to up to +1.0 mbar higher and, for example, up to −1.2 mbar lower. In other words, the pressure of the gas stream flowing through the rotary tube may be below the ambient pressure of the rotary tube when it leaves the rotary tube.

When the intention is not to at least partly recycle the gas stream conducted through the rotary tube, the connection between cyclone (12) and cycle gas compressor (13) is made by the three-way valve principle (26) and the gas stream is conducted directly into the offgas cleaning apparatus (23). The connection to the offgas cleaning apparatus disposed downstream of the cycle gas compressor is in this case likewise made by the three-way valve principle. When the gas stream consists substantially of air, it is in this case aspirated (27) via the cycle gas compressor (13). The connection to the cyclone is made by the three-way valve principle. In this case, the gas stream is preferably sucked through the rotary tube, so that the internal rotary tube pressure is less than the ambient pressure.

In the case of continuous operation of the rotary tube furnace apparatus, the pressure downstream of the rotary tube outlet is advantageously set −0.2 mbar below the external pressure. In the case of batchwise operation of the rotary tube apparatus, the pressure downstream of the rotary tube outlet is advantageously set −0.8 mbar below the external pressure. The slightly reduced pressure serves the purpose of preventing contamination of the ambient air with gas mixture from the rotary tube furnace.

Between the cycle gas compressor and the cyclone are disposed sensors (18) which determine, for example, the ammonia content and the oxygen content in the cycle gas. The ammonia sensor preferably operates by an optical measurement principle (the absorption of light of a certain wavelength correlates proportionally to the ammonia content of the gas) and is appropriately an MCS 100 instrument from Perkin & Elmer. The oxygen sensor is based on the paramagnetic properties of oxygen and is appropriately an Oxymat from Siemens of the Oxymat MAT SF 7MB1010-2CA01 -1AA1-Z type.

Between the diaphragm (15) and the heater (10), gases such as air, nitrogen, ammonia or other gases may be metered into the cycle gas fraction (19) which has actually been recirculated. Frequently, a base load of nitrogen is metered in (20). A separate nitrogen/air splitter (21) may be used to react to the measurement of the oxygen sensor.

The discharged cycle gas fraction (22) (offgas) frequently comprises gases such as $NO_x$, acetic acid, $NH_3$, etc. which are not entirely safe, which is why they are normally removed in an offgas cleaning apparatus (23).

To this end, the offgas is generally initially conducted through a washing column (essentially a column free of internals which contains a separating structured packing upstream of its outlet; the offgas and aqueous spray mist are conducted in countercurrent and in cocurrent (2 spray nozzles having opposite spray direction).

Exiting the washing column, the offgas is conducted into an apparatus which contains a fine dust filter (generally a series of bag filters) from whose interior the penetrant offgas is discharged. Finally, incineration is effected in a muffle furnace.

A sensor (28) from KURZ Instruments, Inc., Monterey (USA) of the 455 Jr model is used to measure and control the flow rate of the gas stream which is fed to the rotary tube and is different to the barrier gas (measurement principle: thermal-convective mass flow measurement using an isothermal anemometer).

In the case of continuous operation, material and gas phase are conducted through the rotary tube furnace in countercurrent.

In connection with this example, nitrogen always means nitrogen having a purity of >99% by volume.

2. Preparation of a precursor composition for the purpose of obtaining a multielement oxide composition of the stoichiometry $Mo_{12}V_3W_{1.2}Cu_{2.4}O_x$ 16.3 kg of copper(ll) acetate hydrate (content: 40.0% by weight of CuO) were dissolved with stirring in 274 l of water at a temperature of 25° C. A clear solution 1 was obtained.

Spatially separately therefrom, 614 l of water were heated to 40° C. and 73 kg of ammonium heptamolybdate tetrahydrate (81.5% by weight of $MoO_3$) was stirred in while maintaining the 40° C. The mixture was then heated with stirring to 90° C. within 30 min and, while retaining this temperature, successively and in the sequence mentioned, 11.3 kg of ammonium metavanadate and 10.7 kg of ammonium paratungstate heptahydrate (88.9% by weight of $WO_3$) was stirred in. A clear solution 2 was obtained.

Solution 2 was cooled to 80° C. and subsequently solution 1 was stirred into solution 2. The resulting mixture was admixed with 130 l of a 25% by weight aqueous $NH_3$ solution which had a temperature of 25° C. With stirring, a clear solution was formed which briefly had a temperature of 65° C. and a pH of 8.5. To this were once again added 20 l of water at a temperature of 25° C. Afterward, the temperature of the resulting solution rose again to 80° C. and the solution was then spray-dried using an S-50-N/R spray drier from Niro-Atomizer (Copenhagen) (gas inlet temperature: 350° C., gas outlet temperature: 110° C). The spray powder had a particle diameter of from 2 to 50 µm. 60 kg of thus obtained spray powder were metered into a VM 160 kneader (Sigma blades) from AMK (Aachener Misch- und Knetmaschinen Fabrik) and kneaded with the addition of 5.5 l of acetic acid (≈100% by weight, glacial acetic acid) and 5.2 l of water (rotation rate of the screws: 20 rpm). After a kneading time of from 4 to 5 minutes, a further 6.5 l of water were added and the kneading process was continued until 30 minutes had elapsed (kneading temperature from approx. 40 to 50° C.). Afterward, the kneaded material was emptied into an extruder and shaped by means of the extruder (from Bonnot Company (Ohio), model: G 103-10/D7A-572K (6" Extruder W Packer) to extrudates (length: 1 -10 cm; diameter 6 mm). On the belt drier, the extrudates were dried at a temperature of 120° C. (material temperature) for 1 h. The dried extrudates formed the precursor composition to be treated thermally.

3. Preparation of the catalytic active composition by thermal treatment of the precursor composition (calcination of the precursor composition) in a rotary tube furnace apparatus The thermal treatment was carried out in the rotary tube furnace described under "B) 1." according to FIG. 1 and under the following conditions:

the thermal treatment was effected batchwise using a material amount of 300 kg which had been prepared as described in "B) 2.";

the inclination angle of the rotary tube to the horizontal was ≈0°;

the rotary tube rotated to the right at 1.5 revolutions/min;

over the entire thermal treatment, a gas stream of 205 m³ (STP)/h was conducted through the rotary tube and (after displacement of the air originally present) had the following composition and was supplemented at its outlet from the rotary tube by a further 25 m³ (STP)/h of barrier gas nitrogen:

80 m³ (STP)/h composed of baseload nitrogen (20) and gases released in the rotary tube, 25 m³ (STP)/h of barrier gas nitrogen (11), 30 m³ (STP)/h of air (splitter (21)); and 70 m³ (STP)/h of recirculated cycle gas (19).

The barrier gas nitrogen was fed at a temperature of 25° C. The mixture of the other gas streams, coming from the heater, was in each case conducted into the rotary tube at the temperature that the material had in each case in the rotary tube.

within 10 h, the material temperature of 25° C. was heated in a substantially linear manner to 300° C.;

subsequently, the material temperature was heated within 2 h in a substantially linear manner to 360° C.;

subsequently, the material temperature was reduced to 350° C. in a substantially linear manner within 7 h;

then the material temperature was heated to 420° C. in a substantially linear manner within 2 h and this material temperature was held over 30 min;

then the 30 m³ (STP)/h of air in the gas stream conducted through the rotary tube were replaced by a corresponding increase in the baseload nitrogen (which ended the procedure of the actual thermal treatment), the heating of the rotary tube was switched off and the material was cooled by switching on the rapid cooling of the rotary tube by aspirating ambient air to a temperature below 100° C. within 2 h and finally to ambient temperature; the gas stream was fed to the rotary tube at a temperature of 25° C.;

over the entire thermal treatment, the pressure (directly) downstream of the rotary tube outlet of the gas stream was 0.2 mbar below the external pressure.

The oxygen content of the gas atmosphere in the rotary tube furnace in all phases of the thermal treatment was 2.99% by volume. Arithmetically averaged over the entire duration of the reductive thermal treatment, the ammonia concentration of the gas atmosphere in the rotary tube furnace was 4% by volume.

Figure 2:
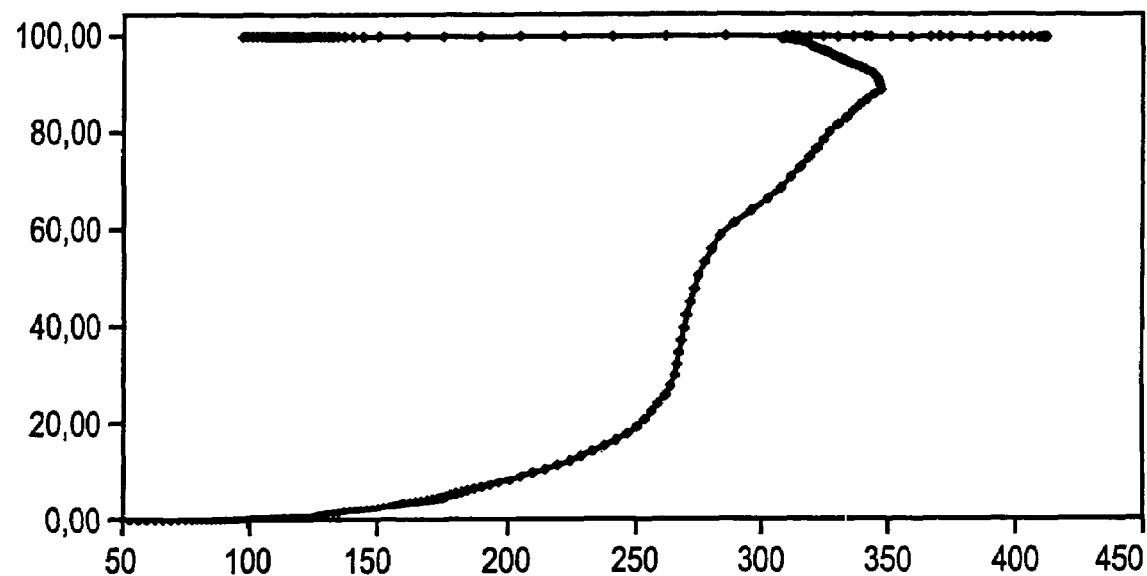
FIG. 2 shows ammonia released as a function of the material temperature as a percentage of the total amount of ammonia released during thermal treatment.

FIG. 2 shows the amount of ammonia released from the precursor composition as a function of the material temperature in °C as a percentage of the total amount of ammonia released from the precursor composition within the overall course of the thermal treatment.

Figure 3:
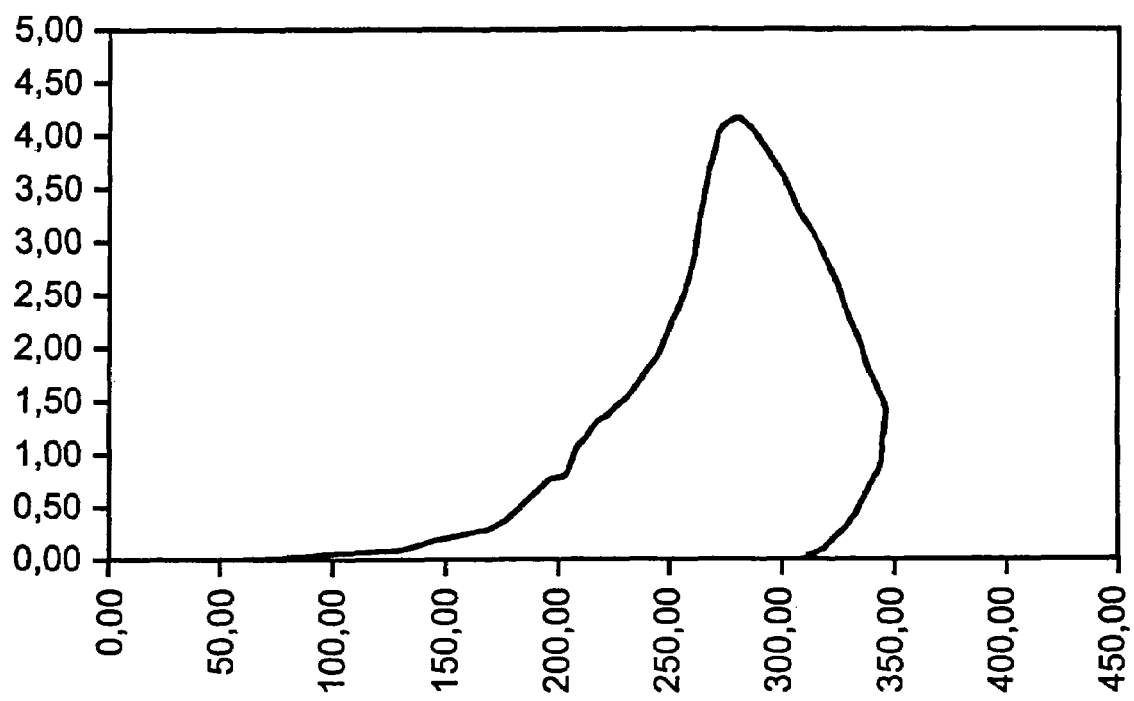
FIG. 3 shows the ammonia concentration in the atmosphere in which thermal treatment was effected during the thermal treatment.

FIG. 3 shows the ammonia concentration of the atmosphere in % by volume in which the thermal treatment was effected as a function of the material temperature in °C during the thermal treatment.

Figure 4:
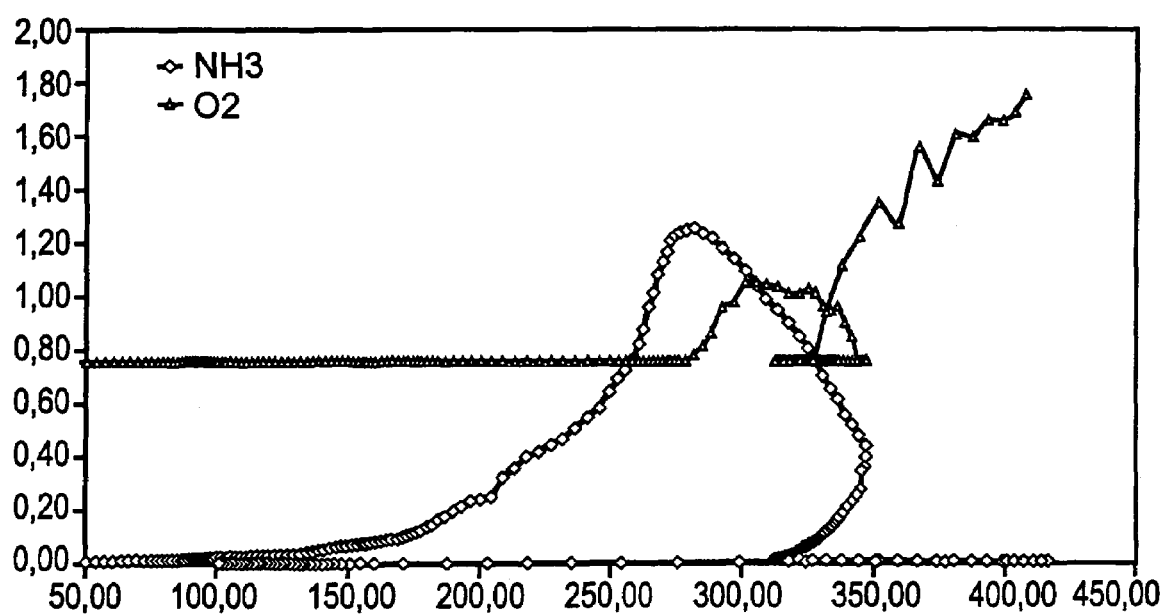
FIG. 4 shows the molar amounts of molecular oxygen and ammonia which were conducted into the rotary tube over the thermal treatment.

FIG. 4 shows, as a function of the material temperature, the molar amounts of molecular oxygen and of ammonia which were conducted into the rotary tube per kg of precursor composition and hour over the thermal treatment with the gas stream.

4. Shaping of the multimetal oxide active composition Th e catalytically active material obtained under "B) 3." was ground by means of a BQ500 Biplex crossflow classifying mill (from Hosokawa-Alpine Augsburg) to give a fine powder of which 50% of the powder particles passed through a sieve of mesh width from 1 to 10 µm and whose proportion of particles of longest dimension above 50 µm was less than 1 %.

The shaping was then effected as follows:

70 kg of annular support bodies (external diameter 7.1 mm, length 3.2 mm, internal diameter 4.0 mm; type C220 steatite from CeramTec having a surface roughness $R_z$ of 45 µm and a total pore volume based on the volume of the support body of ≧1% by volume; cf. DE-A 2135620) were charged into a coating tank (inclination angle 90°; Hicoater from Lodige, Germany) of capacity 200 l. Subsequently, the coating tank was set into rotation at 16 rpm. A nozzle was used to spray from 3.8 to 4.2 liters of an aqueous solution composed of 75% by weight of water and 25% by weight of glycerol onto the support bodies within 25 min. At the same time, 18.1 kg of the ground multimetal oxide active composition (whose specific surface area was 13.8 m²/g) were metered in continuously within the same period via an agitated channel outside the spray cone of the atomizer nozzle. During the coating, the powder supplied was fully taken up on the surface of the support body; no agglomeration of the finely divided oxidic active composition was observed. On completion of addition of active composition powder and water, hot air (approx. 400 m³/h) at 100° C. (alternatively from 80 to 120° C.) was blown into the coating tank at a rotation rate of 2 rpm for 40 min (alternatively from 15 to 60 min). Annular coated catalysts $C_A$ were obtained whose proportion of oxidic active composition based on the overall composition was 20% by weight. The coating thickness, viewed both over the surface of one support body and over the surface of different support bodies, was 170±50 µm.

Figure 5:
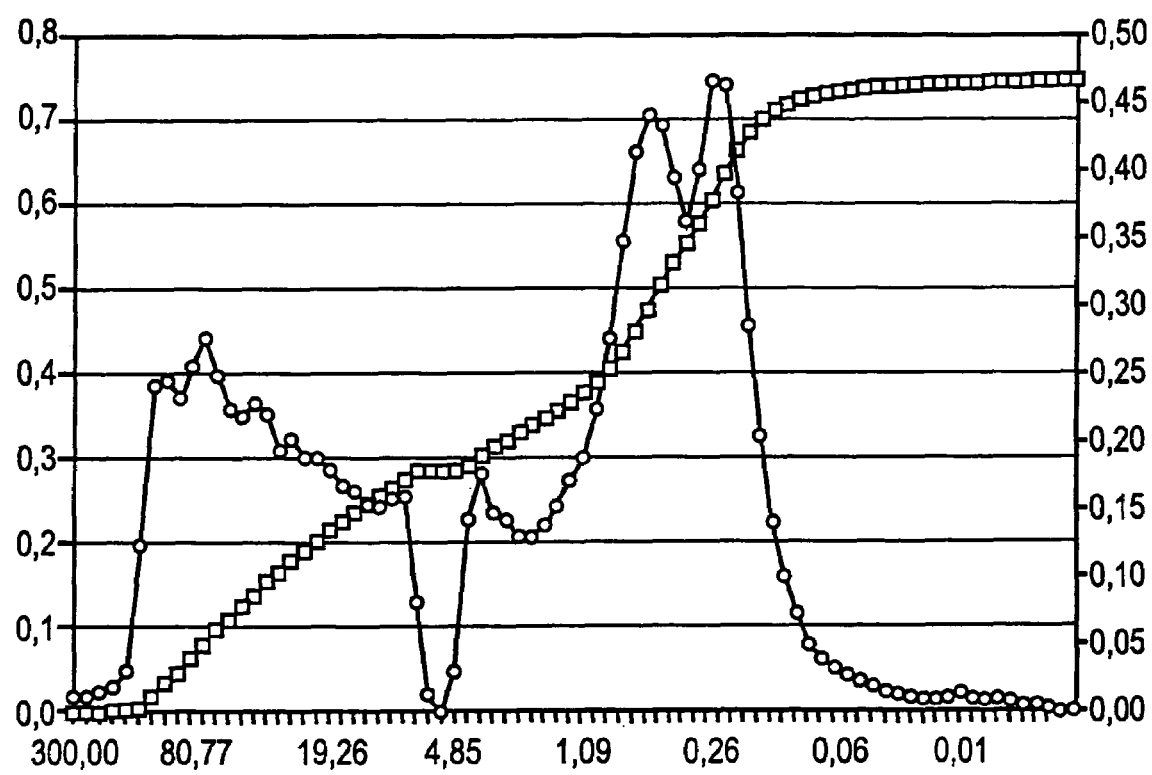
FIG. 5 shows the pore distribution of the ground active composition powder before shaped in Example B.

FIG. 5 also shows the pore distribution of the ground active composition powder before it is shaped. On the abscissa is plotted the pore diameter in µm (logarithmic scale).

On the right ordinate is plotted the logarithm of the differential contribution in m/lg of the particular pore diameter to the total pore volume (O curve). The maximum indicates the pore diameter having the greatest contribution to the total pore volume. On the left ordinate is plotted in ml/g the integral over the individual contributions of the individual pore diameters to the total pore volume (curve). The end point is the total pore volume (unless stated otherwise, all data in this document on determinations of total pore volumes and on diameter distributions to these total pore volumes relates to determinations by the method of mercury porosimetry using the Auto Pore 9220 instrument from Micromeritics GmbH, 4040 Neuss, Germany (bandwidth from 30 Å to 0.3 mm); all data in this document on determinations of specific surface areas or of micropore volumes relate to determinations to DIN 66131 (determination of the specific surface area of solids by Brunauer-Emmet-Teller (BET) gas adsorption ($N_2$)).

Figure 6:
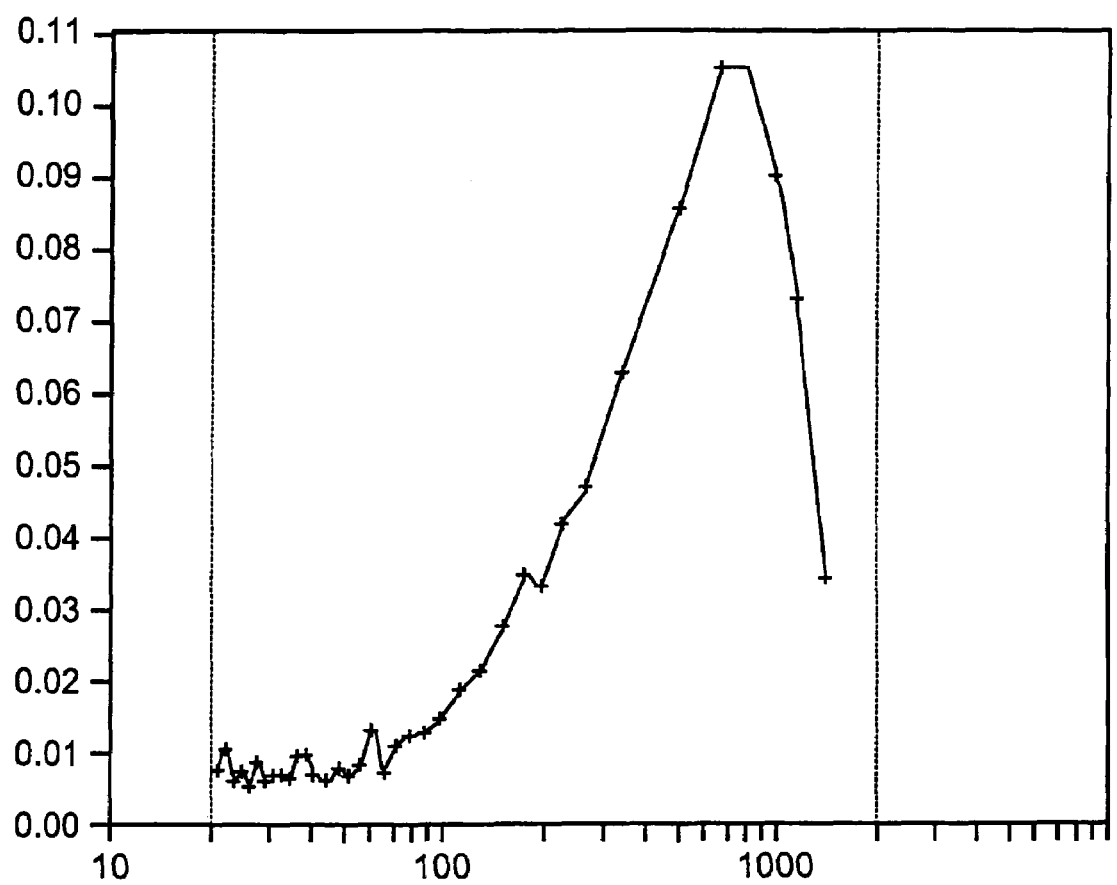
FIG. 6 shows the individual contributions of the individual pore diameters for the active composition before shaped in Example B.

FIG. 6 shows, for the active composition powder before it is shaped, in mVg (ordinate), the individual contributions of the individual pore diameters (abscissa, in angstrom, logarithmic scale) in the micropore range to the total pore volume.

Figure 7:
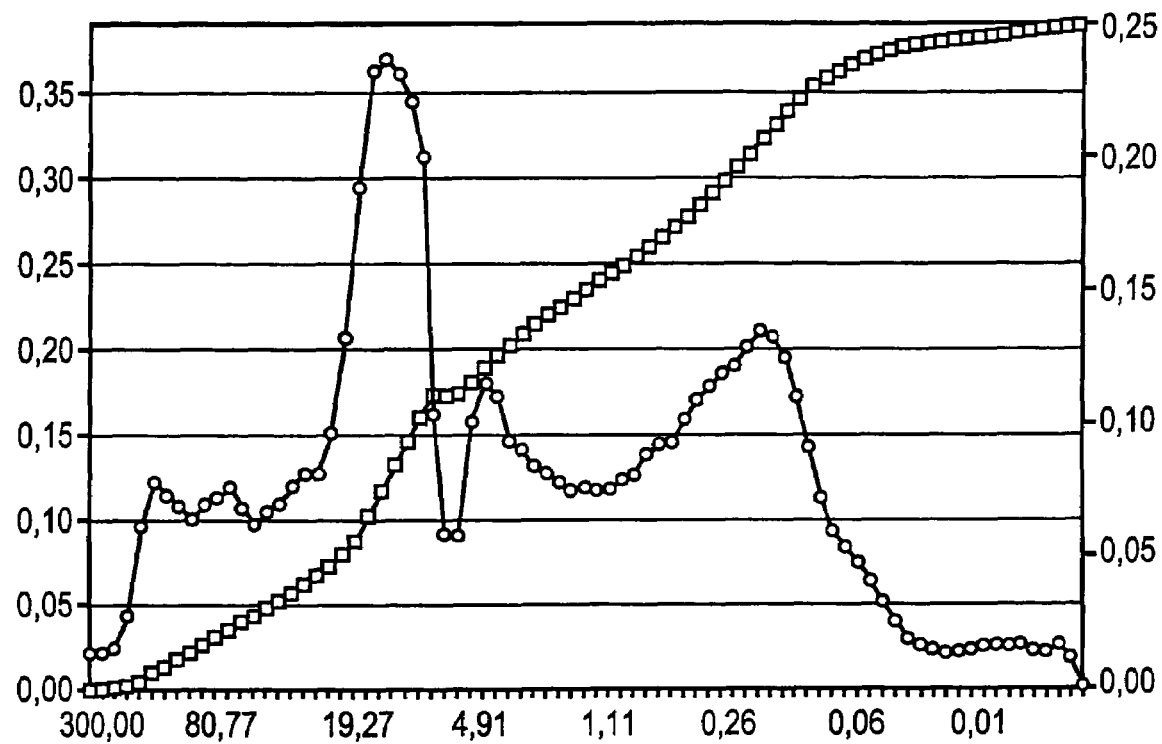
FIG. 7 shows the pore distribution of the ground active composition powder before shaped in Example B for multimetal oxide active composition removed from the annular coated catalyst.

FIG. 7 shows the same as FIG. 5, but for multimetal oxide active composition subsequently removed from the annular coated catalyst $C_A$ by mechanical scraping (its specific surface area was 12.9 m²/g).

Figure 8:
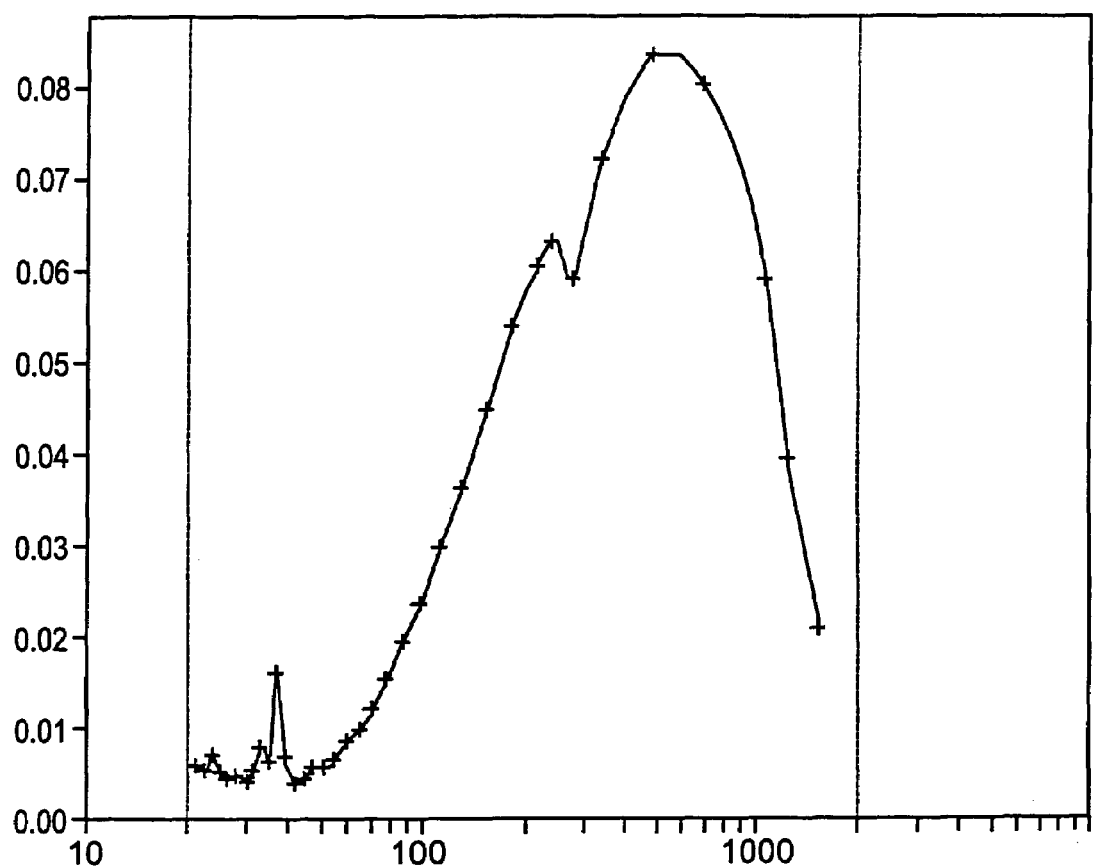
FIG. 8 shows the individual contributions of the individual pore diameters for the active composition before shaped in Example B for multimetal oxide active composition removed from the annular coated catalyst.

FIG. 8 shows the same as FIG. 6, but for multimetal oxide active composition subsequently removed from the annular coated catalyst by mechanical scraping.

C) Performance of a two-stage partial oxidation of propene to acrylic acid (on the industrial scale)

I. Description of the general process conditions in the propene reaction stage (propene→acrolein)

| | |
|---|---|
| Heat exchange medium used: | Salt melt consisting of 60% by weight of potassium nitrate and 40% by weight of sodium nitrite. |
| Material of the catalyst tubes: | ferritic steel. |
| Dimensions of the catalyst tubes: | Length 3200 mm; internal diameter 25 mm; external diameter 30 mm (wall thickness: 2.5 mm). |
| Number of catalyst tubes in the tube bundle: | 25 500. |
| Reactor: | Cylindrical vessel of diameter 6800 mm; annularly arranged tube bundle having a free central space.<br>Diameter of the central free space: 1000 mm. Distance of the outermost catalyst tubes from the vessel wall: 150 mm. Homogeneous catalyst tube distribution in the tube bundle (6 equidistant neighboring tubes per catalyst tube).<br>Catalyst tube pitch: 38 mm.<br>The catalyst tubes were secured and sealed by their ends in catalyst tube plates of thickness 125 mm and opened with their orifices each into a hood connected to the vessel at the upper or lower end. Between the upper hood and the upper catalyst tube plate was disposed, mounted centrally, an impingement plate, toward which the fed reaction gas mixture flowed and was then deflected in a distributive manner to the catalyst tubes.<br>Feed of the heat exchange medium to the tube bundle:<br>The tube bundle was divided by three deflecting plates (thickness in each case 10 mm) mounted in succession between the catalyst tube plates in the longitudinal direction into 4 equidistant (each 730 mm) longitudinal sections (zones). |

The uppermost and the lowermost deflecting plate had annular geometry, the internal annular diameter was 1000 mm and the external annular diameter extended with sealing to the vessel wall. The catalyst tubes were not secured and sealed to the deflecting plates. Rather, a gap having a gap width of <0.5 mm was left in such a way that the transverse flow rate of the salt melt was substantially constant within one zone.

The middle deflecting plate was circular and extended up to the outermost catalyst tubes of the tube bundle.

The recycling of the salt melt was brought about by two salt pumps, each of which supplied one longitudinal half of the tube bundle.

The pumps compressed the salt melt into an annular channel which was arranged at the bottom around the reactor jacket and divided the salt melt over the vessel circumference. The salt melt reached the tube bundle in the lowermost longitudinal section through windows in the reactor jacket. The salt melt then flowed as dictated by the deflecting plates in the sequence from the outside inward,
from the inside outward,
from the outside inward,
from the inside outward, in a substantially meandering manner, viewed over the vessel, from bottom to top. The salt melt collected through windows mounted in the uppermost longitudinal section around the vessel circumference in an annular channel mounted at the top around the reactor jacket and, after cooling to the original inlet temperature, was compressed back into the lower annular channel by the pumps.

The composition of the starting reaction gas mixture 1 (mixture of air, chemical-grade propylene and cycle gas) over the operating time was within the following framework:

from 5 to 7% by volume of chemical-grade propene,
from 10 to 14% by volume of oxygen,
from 1 to 2% by volume of COx,
from 1 to 3% by volume of $H_2O$, and
at least 80% by volume of $N_2$.

| | |
|---|---|
| Reactor charge: | Salt melt and reaction gas mixture were conducted in countercurrent viewed over the reactor. The salt melt entered at the bottom, the reaction gas mixture at the top.<br>The inlet temperature of the salt melt was 337° C. at the start.<br>The outlet temperature of the salt melt was 339° C. at the start.<br>The pump output was 6200 m³ of salt melt/h.<br>The starting reaction gas mixture was fed to the reactor at a temperature of 300° C. |
| Propene loading of the fixed catalyst bed for the propene partial oxidation: | from 100 to 120 l (STP)/l · h |
| Catalyst tube charge with fixed catalyst bed for the propene partial oxidation (from top to bottom): | Zone A: 50 cm<br>Preliminary bed of steatite rings of geometry 7 mm × 7 mm × 4 mm (external diameter × length × internal diameter)<br>Zone B: 100 cm | catalyst charge with a homogeneous mixture of 35% by weight of steatite rings of geometry 5 mm × 3 mm × 2 mm (external diameter × length × internal diameter) and 65% by weight of the unsupported catalyst $C_p$ prepared in A).
Zone C: 170 cm
catalyst charge with the annular (5 mm × 3 mm × 2 mm = external diameter × length × internal diameter) unsupported catalyst $C_p$ prepared in A).

The thermal tubes (their number was 10 which were uniformly distributed in the central region of the tube bundle) were configured and charged as follows: (they were used to determine the hotspot temperature (maximum temperature along a thermal tube) to control the inlet temperature of the salt melt; this is an arithmetic average of independent measurements in the 10 thermal tubes)

Each of the 10 thermal tubes had a central thermowell having 40 temperature measurement points (i.e. each thermal tube contained 40 thermoelements which were integrated into a thermowell at different lengths and thus formed a multithermoelement by which the temperature could be simultaneously determined within the thermal tube at different heights).

At least 13 and at most 30 of the in each case 40 temperature measurement points were in the region of the first meter of the active section of the fixed catalyst bed (in the flow direction of the reaction gas mixture).

The internal diameter of a thermal tube was 27 mm. The wall thickness and the tube material were as in the working tubes.

The external diameter of the thermowell was 4 mm.

The thermal tubes were charged as follows:

A thermal tube was charged with the annular unsupported catalyst $C_p$ prepared in A). In addition, catalyst spall which had been generated from the annular unsupported catalyst $C_p$ and had a longest dimension of from 2 to 3 mm was charged into the thermal tube.

The catalyst spall was charged in homogeneous distribution over the entire active section of the fixed catalyst bed of the particular thermal tube in such a way that the pressure drop of the reaction gas mixture as it passed through the thermal tube corresponded to that as the reaction gas mixture passed through a working tube (for this purpose, from 5 to 20% by weight of catalyst spall were required based on the active section of the fixed catalyst bed (i.e. excluding the inert sections) in the thermal tube). At the same time, the particular total fill height of active and inert sections in the working and thermal tubes was the same and the ratio of the total amount of active composition present in the tube to heat exchange surface area of the tube in working and thermal tubes was set at substantially the same value.

II. Description of the intermediate cooling

The product gas mixture leaving the propene reaction stage at a temperature corresponding substantially to the salt melt outlet temperature was, for the purpose of intermediate cooling, conducted through a one-zone tube bundle heat exchanger made of ferritic steel which was cooled with a salt melt composed of 60% by weight of potassium nitrate and 40% by weight of sodium nitrite and had been flanged directly onto the reactor. The separation of the lower tube plate of the reactor from the upper tube plate of the cooler was 10 cm. The salt melt and the product gas mixture, viewed over the heat exchanger, were conducted in countercurrent. The salt bath itself flowed, in the same manner as in the first-stage one-zone multiple catalyst tube fixed bed reactor, in a meandering manner around the cooling tubes through which the product gas mixture was passed. The length of the cooling tubes was 1.65 m, their internal diameter was 2.6 cm and their wall thickness was 2.5 mm. The number of cooling tubes was 8000. The diameter of the heat exchanger was 7.2 m.

They were distributed uniformly over the cross section with uniform tube pitch.

Into the inlet of the cooling tubes (in flow direction) were introduced spirals of stainless steel whose cross section corresponded virtually to that of the cooling tubes. Their length was from 700 mm to 1000 mm (alternatively, the cooling tubes may be filled with large inert material rings). They served to improve the heat transfer.

The product gas mixture left the intermediate cooler at a temperature of 250° C. Subsequently, compressed air which had a temperature of 140° C. was mixed with it in an amount of about 6700 m³ (STP)/l·h, so as to result in the composition described hereinbelow of the charge gas mixture for the acrolein reaction stage.

The resulting charge gas mixture (starting reaction gas mixture 2) was fed to the one-zone multiple catalyst tube fixed bed reactor of the acrolein reaction stage at a temperature of 220° C.

III. Description of the general process conditions in the acrolein reaction stage (acrolein→acrylic acid)

A one-zone multiple catalyst tube fixed bed reactor was used which had the same design as that of the first stage.

The composition of the charge gas mixture (starting reaction gas mixture 2) was within the following framework over the operating time:

from 4 to 6% by volume of acrolein,
from 5 to 8% by volume of $O_2$,
from 1.2 to 2.5% by volume of $CO_x$,
from 6 to 10% by volume of $H_2O$ and
at least 75% by volume of $N_2$

| Reactor charge: | Salt melt and charge gas mixture were conducted in countercurrent viewed over the reactor. The salt melt entered from the bottom, the charge gas mixture from the top. |
|---|---|

| | |
|---|---|
| | The inlet temperature of the salt melt at the start (on completion of conditioning of the fixed catalyst bed for the acrolein partial oxidation) was approx. 263° C. The accompanying outlet temperature of the salt melt was approx. 265° C. at the start.<br>The pump output was 6200 m³ of salt melt/h.<br>The starting reaction gas mixture was fed to the reactor at a temperature of 240° C. |
| Acrolein loading of the fixed catalyst bed for the acrolein partial oxidation: | from 90 to 110 l (STP)/l · h |
| The catalyst tube charge with fixed catalyst bed for the acrolein partial oxidation (from top to bottom) was: | Zone A:<br>20 cm preliminary bed of steatite rings of geometry 7 mm × 7 mm × 4 mm (external diameter × length × internal diameter).<br>Zone B:<br>100 cm catalyst charge of a homogeneous mixture of 30% by weight of steatite rings of geometry 7 mm × 3 mm × 4 mm (external diameter × length × internal diameter) and 70% by weight of the annular (approx. 7 mm × 3 mm × 4 mm) coated catalyst $C_A$ prepared in B).<br>Zone C:<br>200 cm catalyst charge of the annular (approx. 7 mm × 3 mm × 4 mm) coated catalyst $C_A$ prepared in B). |

The thermal tubes (their number was 10 which were uniformly distributed in the central region of the tube bundle) were configured and charged as follows: 25 (they were used to determine the hotspot temperature (maximum temperature along a thermal tube) to control the inlet temperature of the salt melt; this is an arithmetic average of independent measurements in the 10 thermal tubes)

Each of the 10 thermal tubes had a central thermowell having 40 30 temperature measurement points (i.e. each thermal tube contained 40 thermoelements which were integrated into a thermowell at different lengths and thus formed a multithermoelement by which the temperature could be simultaneously determined within the thermal tube at different heights).

At least 13 and at most 30 of the in each case 40 temperature measurement points were in the region of the first meter of the active section of the fixed catalyst bed (in the flow direction of the reaction gas mixture).

The internal diameter of a thermal tube was 27 mm. The wall thickness and the tube material were as in the working tubes.

The external diameter of the thermowell was 4 mm.

The thermal tubes were charged as follows:

A thermal tube was charged with the annular coated catalyst $C_A$ prepared in B). In addition, spherical coated catalyst (same active composition as the annular coated catalyst, the diameter of the Steatite C220 (CeramTec) support spheres was 2-3 mm; the active composition fraction was 20% by weight, the preparation was as described for the annular coated catalyst $C_A$, except that the binder was an appropriate amount of water) was charged into the thermal tube.

The spherical coated catalyst was charged in homogeneous distribution over the entire active section of the fixed catalyst bed of the particular thermal tube in such a way that the pressure drop of the reaction gas mixture as it passed through the thermal tube corresponded to that when the reaction gas mixture passed through a working tube (based on the active section of the fixed catalyst bed (i.e. excluding the inert sections); for this purpose, from 5 to 20% by weight of spherical coated catalyst were required in the thermal tube). At the same time, the particular total fill height of active and inert sections in the working and thermal tubes was the same and the ratio of the total amount of active composition present in the tube to heat exchange surface area of the tube in working or thermal tubes was set at the same value.

III. Long-term operation (results)

The fixed catalyst bed of the tube bundle reactor for the propene partial oxidation to acrolein has been freshly charged 1.5 years before the catalyst bed of the tube bundle reactor for the acrolein partial oxidation to acrylic acid.

The target conversion for the propene to be converted in single pass of the starting reaction gas mixture 1 through the fixed catalyst bed of the propene oxidation stage was set to 97.5 mol %.

Gradual increase in the inlet temperature of the salt melt into the reactor of the propene reaction stage allowed this conversion valve to be maintained over time in the course of continuous performance of the process.

The target conversion for the acrolein to be converted in single pass of the starting reaction gas mixture 2 through the fixed catalyst bed of the acrolein reaction stage was set to 99.3 mol %.

Gradual increase in the inlet temperature of the salt melt into the reactor of the acrolein reaction stage allowed this conversion value to be maintained over time in the course of continuous performance of the process.

About once per calendar month, the partial oxidation was interrupted (the increase in the inlet temperature of the salt melt into the reactor of the acrolein reaction stage up to the about monthly interruption was always $\geq 0.3°$ C. and $\leq 4°$ C.; in the case of the reactor for the propene reaction stage, the increased values required about every month were $\geq 0.5°$ C.), the inlet temperature of the salt melt last employed in the particular reaction stage and in the intermediate cooler was retained and a gas mixture G composed of 6% by volume of $O_2$ and 95% by volume of $N_2$ was conducted through the entire reaction system for a period $t_G$ of from 24 h to 48 h at an hourly space velocity on the fixed catalyst bed of the propene reaction stage of 30 l (STP)/l·h. Afterward, the partial oxidation was continued and the inlet temperature of the salt melt into the particular reaction stage adjusted in such a way that the target conversion of the particular reaction stage was still achieved.

After operation as described for more than two years (calculated from fresh charging of the propene reaction stage) of the reaction system, the operating conditions and results, after the gas mixture G had been passed through the reaction system and the partial oxidation had subsequently been continued, after the 13th operating day were as follows (d=operating days after continuation of the partial oxidation; SV=hourly space velocity on the propene reaction stage of propene in I (STP)/I·h; $C^{pro}$=propene conversion based on single pass in mol %; $C^{acr}$=acrolein conversion based on single pass in mol %; $Y^{AA}$=yield of acrylic acid based on single pass and propene converted in mol %; $A^{CO}$=undesired secondary yield of carbon oxides in mol % based on single pass and converted propene; $T^1$=salt bath inlet temperature in the propene reaction stage in ° C.; $T^2$=salt bath inlet temperature in the acrolein reaction stage in ° C.; $P^1$=working pressure at the inlet into the propene reaction stage in mbar; $P^2$=working pressure at the inlet into the acrolein reaction stage in mbar):

| d  | SV    | $Y^{AA}$ | $C^{acr}$ | $C^{pro}$ | $Y^{CO}$ | $T^1$ | $T^2$ | $P^1$ | $P^2$ |
|----|-------|------|------|------|------|-------|-------|------|------|
| 13 | 112.9 | 89.8 | 99.3 | 97.7 | 5.21 | 348.1 | 269.5 | 2270 | 1810 |
| 14 | 112.8 | 89.5 | 99.2 | 97.5 | 5.28 | 348.1 | 270.1 | 2265 | 1805 |
| 15 | 110.6 | 89.4 | 99.4 | 97.4 | 5.3  | 348   | 270.1 | 2268 | 1802 |
| 16 | 113.5 | 89.7 | 99.3 | 97.5 | 5.17 | 348   | 270.1 | 2267 | 1809 |
| 17 | 113.3 | 89.7 | 99.3 | 97.5 | 5.17 | 348.1 | 270.1 | 2268 | 1809 |
| 18 | 113.4 | 89.7 | 99.1 | 97.5 | 5.14 | 348   | 270.1 | 2265 | 1809 |
| 19 | 113   | 89.6 | 99.1 | 97.4 | 5.18 | 348   | 270.1 | 2270 | 1807 |
| 20 | 113.2 | 89.6 | 99.3 | 97.4 | 5.15 | 348   | 270.1 | 2269 | 1805 |

(=comparative example)

After the 20th operating day, the gas mixture G was again conducted as described through the reaction system and the partial oxidation was subsequently continued as described, but with the difference that, downstream of the outlet of the tube bundle reactor for the partial oxidation of acrolein to acrylic acid, for the purpose of increasing the working pressure, a perforated diaphragm was installed. The diameter of the perforated diaphragm was 1.23 m. It contained 37 uniformly distributed holes whose diameter were a uniform 9 cm. After the 13$^{th}$ operating day (calculated from continuation of the partial oxidation), the operating conditions and results were as follows:

| d  | SV    | $Y^{AA}$ | $C^{acr}$ | $C^{pro}$ | $Y^{CO}$ | $T^1$ | $T^2$ | $P^1$ | $P^2$ |
|----|-------|------|------|------|------|-------|-------|------|------|
| 13 | 112.9 | 89.1 | 99.2 | 97.3 | 5.52 | 333.8 | 268.7 | 2420 | 2178 |
| 14 | 113.4 | 89.5 | 99.4 | 97.7 | 5.56 | 336.4 | 268.3 | 2425 | 2180 |
| 15 | 112.8 | 89.7 | 99.3 | 97.7 | 5.45 | 336.4 | 268.4 | 2425 | 2181 |
| 16 | 113.1 | 89.5 | 99.2 | 97.6 | 5.48 | 336.4 | 268.4 | 2421 | 2182 |
| 17 | 113.1 | 89.7 | 99.1 | 98   | 5.66 | 339   | 268.6 | 2420 | 2177 |
| 18 | 113.1 | 89.6 | 99.5 | 97.9 | 5.6  | 338.5 | 268.6 | 2422 | 2180 |
| 19 | 113   | 89.6 | 99.2 | 97.8 | 5.52 | 338.5 | 268.6 | 2424 | 2181 |
| 20 | 113.4 | 89.6 | 99.3 | 97.9 | 5.62 | 339   | 268.8 | 2424 | 2181 |

(=example)

The comparison of the values of $T^1$ in the example under the elevated working pressure $P^1$ at the same propene conversion shows a distinctly reduced salt bath inlet temperature into the reactor of the propene reaction stage without it being accompanied by a significant increase in the $CO_X$ by-product formation. In the acrolein reaction stage, the activity-enhancing effect of the increase in the working pressure is likewise clearly recognizable. However, since the catalyst bed of the acrolein reaction stage was brought onstream 1.5 years after the catalyst bed of the propene reaction stage, the deactivation of the catalyst bed of the acrolein stage is not as far advanced, which is why the effect of the increase in the working pressure is not yet as marked.

D) Performance of a two-stage partial oxidation of propene to acrylic acid (on the laboratory scale)

I. Description of the experimental arrangement for the two reaction stages

Propene reaction stage

A reaction tube (V2A steel; external diameter 30 mm, wall thickness 2 mm, internal diameter 26 mm, a centered thermowell (to accommodate a thermoelement) of external diameter 4 mm, length: 320 cm) was charged from top to bottom as follows:

Section 1: length 50 cm
steatite rings of geometry 7 mm × 7 mm × 4 mm (external diameter × length × internal diameter) as a preliminary bed.
Section 2: length 100 cm
Catalyst charge of a homogeneous mixture of steatite rings of geometry 5 mm × 3 mm × 2 mm (external diameter × length × internal diameter) and 70% by weight of annular unsupported catalyst $C_p$ (prepared as in A)).
Section 3: length 170 cm
Catalyst charge of exclusively annular unsupported catalyst $C_p$ as per section 2.

The reaction tube was thermostatted in countercurrent by means of a nitrogen-sparged salt bath (53% by weight of potassium nitrate, 40% by weight of sodium nitrite and 7% by weight of sodium nitrate).

Acrolein reaction stage

A reaction tube (V2A steel; external diameter 30 mm, wall thickness 2 mm, internal diameter 26 mm, a centered thermowell (to accommodate a thermoelement) of external diameter 4 mm, length: 320 cm) was charged from top to bottom as follows:

Section 1: length 20 cm
Preliminary bed of steatite rings of geometry 7 mm × 7 mm × 4 mm (external diameter × length × internal diameter).
Section 2: length 100 cm
Catalyst charge of a homogeneous mixture of 30% by weight of steatite rings of geometry 7 mm × 3 mm × 4 mm (external diameter × length × internal diameter) and 70% by weight of the annular coated catalyst $C_A$ (prepared as in B)).
Section 3: length 200 cm
Catalyst charge of exclusively annular coated catalyst $C_A$ as per section 2.

The reaction tube was thermostatted in countercurrent by means of a nitro-gen-sparged salt bath (53% by weight of potassium nitrate, 40% by weight of sodium nitrite and 7% by weight of sodium nitrate).

Between the two reaction stages was disposed an intermediate cooler charged with inert material, through which the product gas mixture of the first reaction stage was conducted and cooled to a temperature of 250° C. by indirect cooling.

The first reaction stage (propene→acrolein) was charged continuously with a starting reaction gas mixture of the following composition:

from 5.5 to 5.7% by volume of polymer-grade propene,
from 3 to 3.2% by volume of $H_2O$,
from 1 to 2% by volume of $CO_x$,
from 0.01 to 0.02% by volume of acrolein,
from 10.4 to 10.6% by volume of $O_2$ and,
as the remainder at 100% by volume, molecular nitrogen.

The hourly space velocity on the catalyst charge of propene was selected at 130 l (STP)/l·h. The saltbath temperature of the first reaction stage was $T^1$ (° C.). The saltbath temperature of the second reaction stage (acrolein→acrylic acid) was $T^2$ (° C.). Sufficient compressed air which had a temperature of 140° C. was added to the product gas mixture leaving the intermediate cooler at a temperature of 250° C. that a starting reaction gas mixture was fed to the second reaction stage in which the ratio of molecular oxygen to acrolein (ratio of the percentages by volume) was 1.3. Downstream of the outlet of the second reaction stage was disposed a throttle apparatus which enabled the working pressure to be regulated.

Depending on the working pressure (specified in each case is the pressure in bar directly upstream of the first reaction stage), $T^1$ and $T^2$ were each adjusted in such a way that the propene conversion was 97.5 mol % and the acrolein conversion 99.3 mol % (based in each case on single pass of the reaction gas mixture through the reaction system).

Depending on the working pressure, the following results of the table were obtained. The results are based on a reaction operation after a preceding uninterrupted operating time of 100 h at a working pressure of 1.1 bar and the same conversions.

The temperatures $T^{1max}$ and $T^{2max}$ are the maximum reaction temperatures in ° C. in the particular reaction stage. $\Delta P^1$ and $\Delta P^2$ are the pressure drops suffered in the particular reaction stage in bar.

TABLE

| Working pressure [bar] | $T^1$ [° C.] | $T^{1max}$ [° C.] | $T^2$ [° C.] | $T^2max$ [° C.] | $\Delta P^1$ [bar] | $\Delta P^2$ [bar] |
|---|---|---|---|---|---|---|
| 1.1 | 334 | 382 | 273 | 308 | 0.52 | 0.30 |
| 1.57 | 328 | 380 | 268 | 311 | 0.41 | 0.21 |
| 1.93 | 320 | 382 | 260 | 284 | 0.33 | 0.17 |

U.S. Provisional Patent Application No. 60/572,124, filed on May 19, 2004, is incorporated into the present application by literature reference. With regard to the abovementioned teachings, numerous alterations and deviations from the present invention are possible. It can therefore be assumed that, within the scope of the appended claims, the invention may be performed differently to the way specifically described herein.

What is claimed is:

1. A process for the long-term operation of a heterogeneously catalyzed gas phase partial oxidation of at least one organic compound in at least one oxidation reactor, in which a starting reaction gas mixture comprising the at least one organic compound, molecular oxygen and at least one inert diluent gas is passed through at least one catalyst bed at elevated temperature, which comprises, in order to counteract the deactivation of the at least one catalyst bed, increasing the working pressure in the gas phase, based on an identical hourly space velocity on the at least one catalyst bed of starting reaction gas mixture in l (STP)/l·h, during the operating time of the catalyst bed.

2. The process according to claim 1, wherein the at least one organic compound is at least one compound selected from the group consisting of propylene, acrolein, 1 butene, 2 butene, ethane, benzene, m-xylene, p-xylene, isobutene, isobutane, tert-butanol, isobutyraldehyde, methyl ether of tert-butanol, o-xylene, naphthalene, butadiene, ethylene, propylene, propane and methacrolein.

3. The process according to claim 1 or 2, wherein the at least one oxidation reactor is a tube bundle reactor and the catalyst bed is a fixed catalyst bed.

4. A process according to claim 1, wherein the heterogeneously catalyzed gas phase partial oxidation of at least one organic compound is two-stage partial oxidation of propene to acrylic acid.

5. The process according to claim 1, wherein the increasing in the working pressure in the gas phase is at least 25 mbar.

6. The process according to claim 1, wherein the increasing in the working pressure in the gas phase is from 50 to 3000 mbar.

7. The process according to claim 1, wherein the increasing in the working pressure in the gas phase is undertaken continuously and as a function of the deactivation rate of the at least one catalyst bed.

8. The process according to claim 1, wherein the increasing in the working pressure in the gas phase is undertaken in stages.

9. The process according to claim 1, wherein the at least one organic compound is propylene and an active composition of the catalysts of the at least one catalyst bed is a multielement oxide comprising the elements molybdenum and/or tungsten, and at least one selected from the group consisting of the elements bismuth, tellurium, antimony, tin and copper.

10. The process according to claim 1, wherein the at least one organic compound is acrolein and active composition of the catalysts of the at least one catalyst bed is a multielement oxide comprising the elements Mo and V.

11. The process according to claim 1, wherein a pressure-regulating apparatus is mounted downstream of an outlet of the at least one oxidation reactor.

12. The process according to claim 11, wherein the pressure-regulating apparatus is one selected from the group consisting of a throttle valve, a vane regulator and a perforated diaphragm.

* * * * *